(12) United States Patent
Jayawickramarajah et al.

(10) Patent No.: US 8,877,908 B2
(45) Date of Patent: Nov. 4, 2014

(54) STIMULUS-RESPONSIVE APTA CHELAMERS

(75) Inventors: Janarthanan Jayawickramarajah, New Orleans, LA (US); David Calvin Harris, Chicago, IL (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 886 days.

(21) Appl. No.: 13/003,047

(22) PCT Filed: Jul. 10, 2009

(86) PCT No.: PCT/US2009/050217
§ 371 (c)(1),
(2), (4) Date: Apr. 19, 2011

(87) PCT Pub. No.: WO2010/006238
PCT Pub. Date: Jan. 14, 2010

(65) Prior Publication Data
US 2011/0190483 A1    Aug. 4, 2011

Related U.S. Application Data

(60) Provisional application No. 61/080,214, filed on Jul. 11, 2008.

(51) Int. Cl.
| | | |
|---|---|---|
| C07H 21/04 | (2006.01) | |
| C07F 9/6561 | (2006.01) | |
| C12N 15/115 | (2010.01) | |
| C07D 235/06 | (2006.01) | |

(52) U.S. Cl.
CPC .......... *C07F 9/65616* (2013.01); *C12N 15/115* (2013.01); *C07D 235/06* (2013.01)
USPC ...................................... 536/23.1

(58) Field of Classification Search
None
See application file for complete search history.

(56) References Cited

U.S. PATENT DOCUMENTS

2006/0088864 A1*  4/2006  Smolke et al. ............... 435/6

OTHER PUBLICATIONS

D. Calvin Harris et al., "DNA-Small Molecule Chimera with Responsive Protein⁻ Binding Ability", J. Am. Ceem. Soc. 2008, 130, pp. 14950-14951, Published on Web: Oct. 15, 2008; See Abstract and Scheme 1.
Subramanian Balamurugan et al., "Surface immobilization methods for aptamer : diagnostic applications", Anal Bioanal Chem (2008) 390 pp. 1009-1021, Published on Wcb: Sep. 23, 2007 See Abstract and Scheme 2.
E.B. Starikov et al., "Structural basis of biotin.RNA aptamer binding: a theoretical study", Chemical Physics Letters 363 (2002) pp. 39-44, Sep. 2, 2002 See Abstract and Fig. 1.
Yoshihiro IT et al., "In Vitro Selection of RNA Aptamers Carrying Multiple Biotin Groups in the Side Chains", Bioconjugate Chem. 2001, 12, pp. 850-854 Published on Web: Sep. 22, 2001 See Abstract and Fig. 6.
June Hyung Lee et al., "Interaction of C5 protein with RNA aptamers selected by SELEX", Nucleic Acids Research, 2002, vol. 30, No. 24, pp. 5360-5368 See Abstract and Introduction.
Zehui Cao et al., "Molecular Beacon Aptamers for Protein Monitoring in Real-Time and in Homogeneous Solutions", Current Proteomics, 2005, 2, pp. 31-40 See Abstract and Introduction.
Shinsuke Sando et al., "Light-Up Hoechst.DNA AptamerPair : Generation of an Aptamer-Selective Fluorophore from a Conventional DNA-Staining Dye", ChemBioChem 2007, vol. 8, issue 15 pp. 1795-1803, Published On Web : Sep. 5, 2007 See Abstract and Introduction.
International Search Report for PCT/US2009/050217 dated May 27, 2010.

* cited by examiner

*Primary Examiner* — Tracy Vivlemore
(74) *Attorney, Agent, or Firm* — Miles and Stockbridge

(57) ABSTRACT

Disclosed are apta-chelamers comprising aptamer domains tethered to rationally designed synthetic protein-binding modules, and methods of designing and making the same. Also disclosed are stimulus-responsive apta-chelamers capable of simultaneously or sequentially binding (and, thus, inhibiting) two protein targets.

9 Claims, 27 Drawing Sheets

● = guanine   ↓ = synthetic protein binding element

= guanine quartet

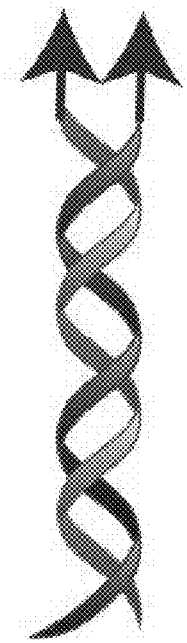
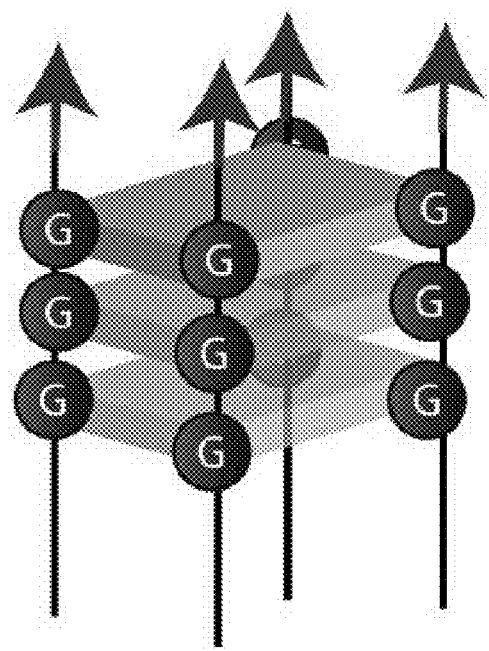
FIG. 3A                    FIG. 3B
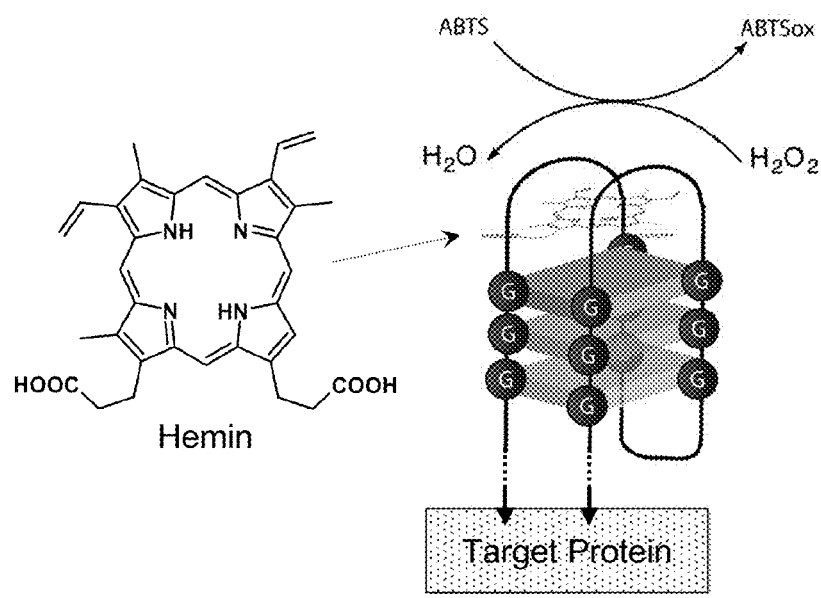
FIG. 4

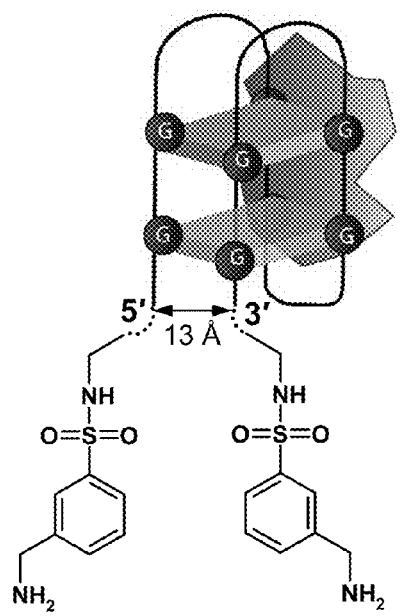 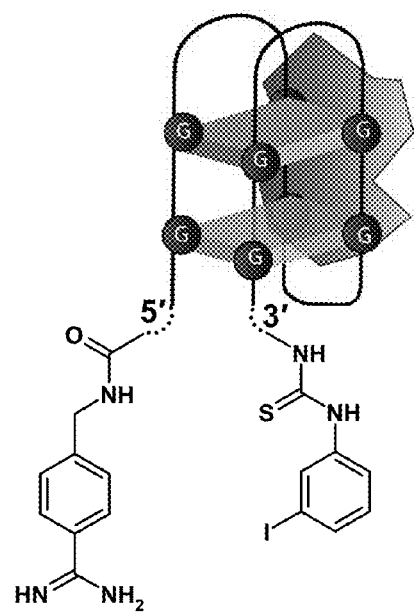
FIG. 6A  FIG. 6B
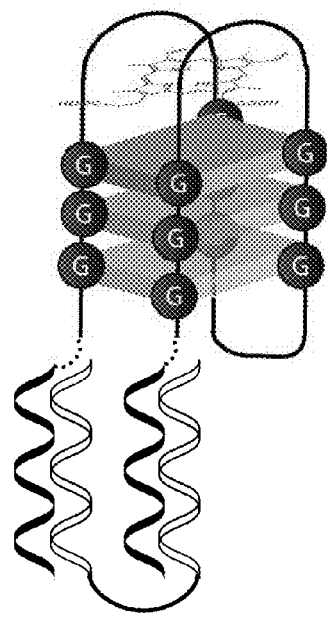
FIG. 6C

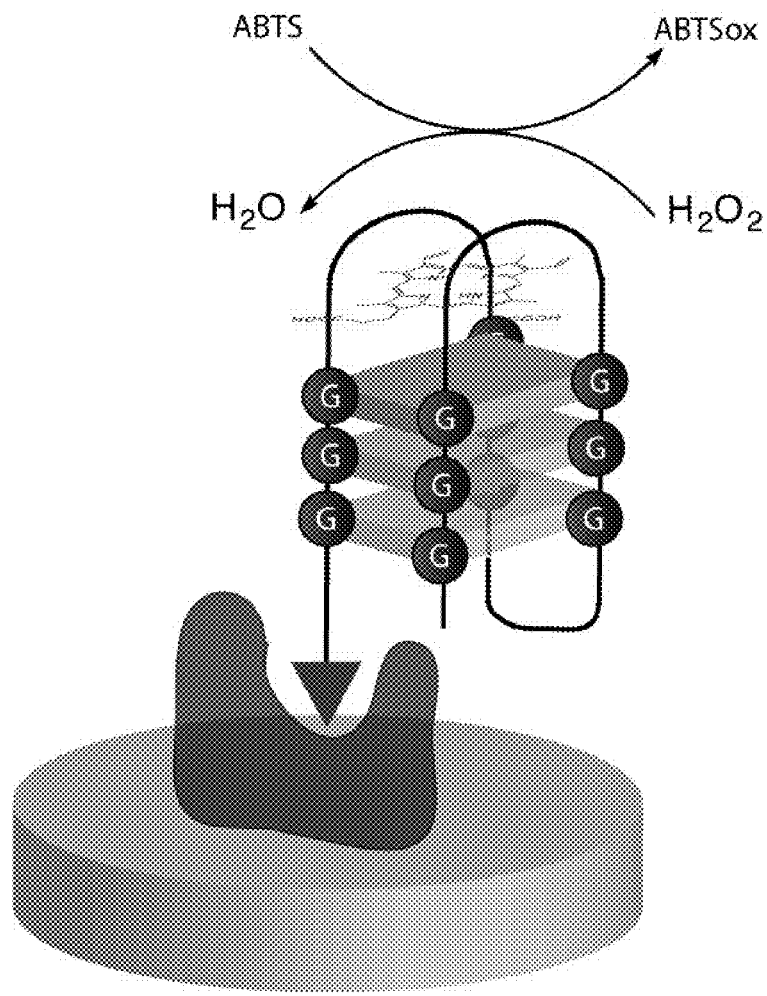
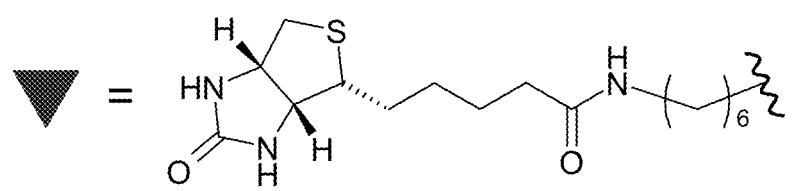
FIG. 28

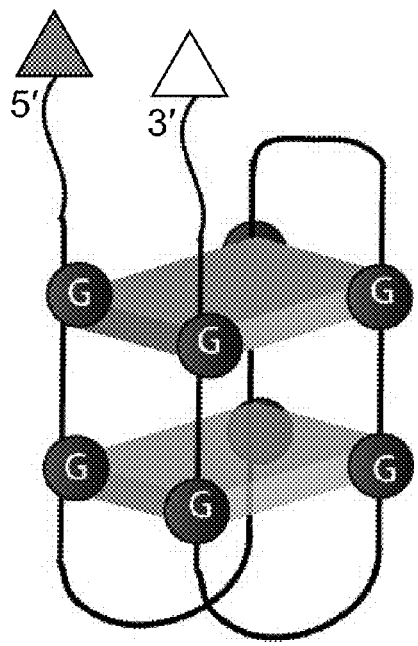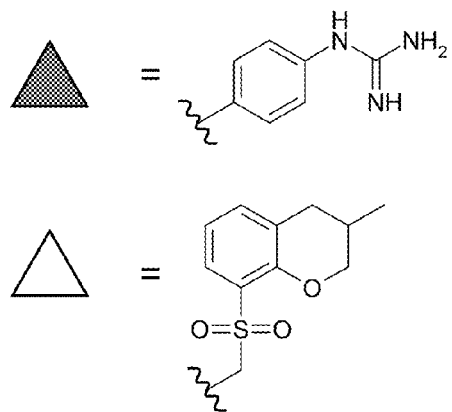
FIG. 29

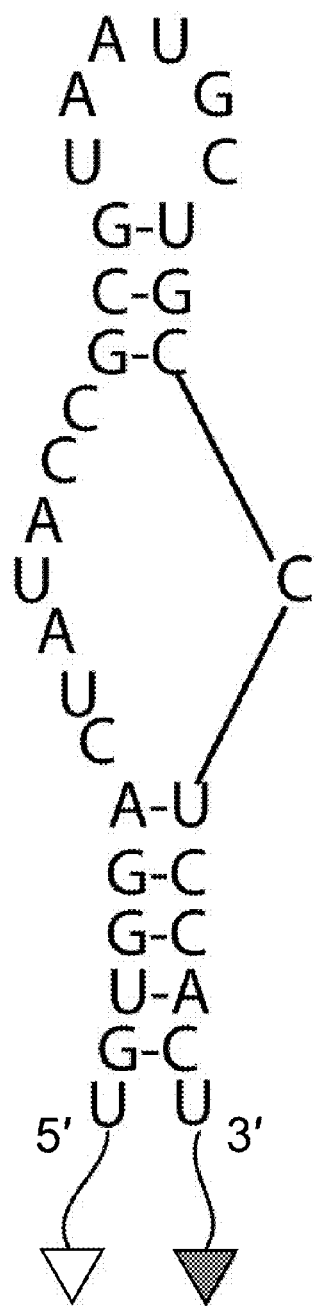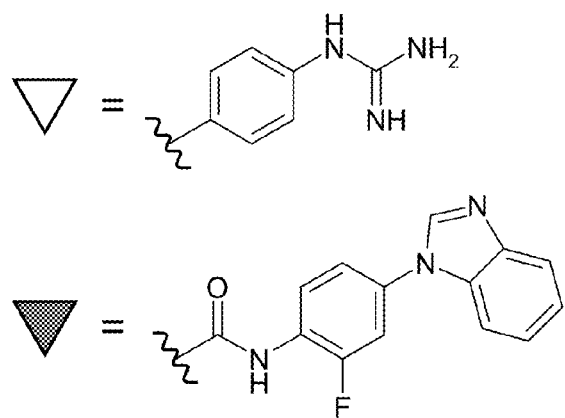
FIG. 31

SEQUENCE LISTING

```
<160> NUMBER OF SEQ ID NOS: 21

<210> SEQ ID NO 1
<211> LENGTH: 18
<212> TYPE: DNA
<213> ORGANISM: Artificial Sequence
<220> FEATURE:
<223> OTHER INFORMATION: Thrombin binding aptamer bearing 5' dT
      conjugated to fluorescein
<220> FEATURE:
<221> NAME/KEY: misc_feature
<222> LOCATION: (1)..(1)
<223> OTHER INFORMATION: may bear optional fluorescein moiety

<400> SEQUENCE: 1
```
ttggttggtg tggttggt                                              18

<210> SEQ ID NO 2
<211> LENGTH: 17
<212> TYPE: DNA
<213> ORGANISM: Artificial Sequence
<220> FEATURE:
<223> OTHER INFORMATION: ODN 5

<400> SEQUENCE: 2
accaaccaca ccaacca                                               17

<210> SEQ ID NO 3
<211> LENGTH: 18
<212> TYPE: DNA
<213> ORGANISM: Artificial Sequence
<220> FEATURE:
<223> OTHER INFORMATION: ODN 6

<400> SEQUENCE: 3
ttggttggtg tggttggt                                              18

<210> SEQ ID NO 4
<211> LENGTH: 17
<212> TYPE: DNA
<213> ORGANISM: Artificial Sequence
<220> FEATURE:
<223> OTHER INFORMATION: TBA

<400> SEQUENCE: 4
tggttggtgt ggttggt                                               17

<210> SEQ ID NO 5
<211> LENGTH: 17
<212> TYPE: DNA
<213> ORGANISM: Artificial Sequence
<220> FEATURE:
<223> OTHER INFORMATION: ODN 7, bearing TAMRA-X at 3' end

<400> SEQUENCE: 5
accaaccaca ccaacca                                               17

<210> SEQ ID NO 6
<211> LENGTH: 15
<212> TYPE: DNA
<213> ORGANISM: Artificial Sequence
<220> FEATURE:
<223> OTHER INFORMATION: Core thrombin binding aptamer

<400> SEQUENCE: 6
ggttggtgtg gttgg                                                 15

<210> SEQ ID NO 7
<211> LENGTH: 18
<212> TYPE: DNA
<213> ORGANISM: Artificial Sequence
<220> FEATURE:
<223> OTHER INFORMATION: ODN 4

<400> SEQUENCE: 7
ttggttggtg tggttggt                                              18

<210> SEQ ID NO 8
<211> LENGTH: 18
<212> TYPE: DNA

```
<213> ORGANISM: Artificial Sequence
<220> FEATURE:
<223> OTHER INFORMATION: Internal standard

<400> SEQUENCE: 8
gtgggtaggg cgggttgg                                                    18

<210> SEQ ID NO 9
<211> LENGTH: 19
<212> TYPE: DNA
<213> ORGANISM: Artificial Sequence
<220> FEATURE:
<223> OTHER INFORMATION: Hemin binding aptamer

<400> SEQUENCE: 9
tgggtagggc gggttgggt                                                   19

<210> SEQ ID NO 10
<211> LENGTH: 17
<212> TYPE: DNA
<213> ORGANISM: Artificial Sequence
<220> FEATURE:
<223> OTHER INFORMATION: Core hemin binding aptamer

<400> SEQUENCE: 10
gggtagggcg ggttggg                                                     17

<210> SEQ ID NO 11
<211> LENGTH: 32
<212> TYPE: RNA
<213> ORGANISM: Artificial
<220> FEATURE:
<223> OTHER INFORMATION: Coagulation factor IXa responsive aptamer

<400> SEQUENCE: 11
uguggacuau accgcguaau gcugccucca cu                                    32

<210> SEQ ID NO 12
<211> LENGTH: 29
<212> TYPE: RNA
<213> ORGANISM: Artificial
<220> FEATURE:
<223> OTHER INFORMATION: VegF responsive aptamer

<400> SEQUENCE: 12
ucggaaucag ugaaugcuua uacauccgu                                        29

<210> SEQ ID NO 13
<211> LENGTH: 36
<212> TYPE: RNA
<213> ORGANISM: Artificial
<220> FEATURE:
<223> OTHER INFORMATION: TAR (trans-activating element of the HIV-1
      genome) responsive aptamer

<400> SEQUENCE: 13
uggagcuccc agacgaccgg ucggcuggga gcuccu                                36

<210> SEQ ID NO 14
<211> LENGTH: 31
<212> TYPE: RNA
<213> ORGANISM: Artificial
<220> FEATURE:
<223> OTHER INFORMATION: NF kappa B p50 responsive aptamer

<400> SEQUENCE: 14
```
ucauacuuga aacuguaagg uuggcguaug u         31

<210> SEQ ID NO 15
<211> LENGTH: 24
<212> TYPE: RNA
<213> ORGANISM: artificial
<220> FEATURE:
<223> OTHER INFORMATION: Splicesome U2B''-U2A' proteins (U1 snRNA
      hairpin II) responsive aptamer

<400> SEQUENCE: 15
uuuauccauu gcacuccgga uguu         24

<210> SEQ ID NO 16
<211> LENGTH: 25
<212> TYPE: RNA
<213> ORGANISM: artificial
<220> FEATURE:
<223> OTHER INFORMATION: Splicesome U2B''-U2A' proteins (U1 snRNA
      hairpin IV) responsive aptamer

<400> SEQUENCE: 16
uccugguauu gcaguaccuc caggu         25

<210> SEQ ID NO 17
<211> LENGTH: 33
<212> TYPE: RNA
<213> ORGANISM: artificial
<220> FEATURE:
<223> OTHER INFORMATION: TAR HIV1 responsive aptamer

<400> SEQUENCE: 17
uggccagauc ugagccuggg agcucucugg ccu         33

<210> SEQ ID NO 18
<211> LENGTH: 30
<212> TYPE: RNA
<213> ORGANISM: artificial
<220> FEATURE:
<223> OTHER INFORMATION: TAR BIV responsive aptamer

<400> SEQUENCE: 18
uggcucgugu agcucauuag cuccgagccu         30

<210> SEQ ID NO 19
<211> LENGTH: 37
<212> TYPE: RNA
<213> ORGANISM: artificial
<220> FEATURE:
<223> OTHER INFORMATION: HIV1 RRE responsive aptamer

<400> SEQUENCE: 19
uggcuggacu cguacuucgg uacuggagaa acagccu         37

<210> SEQ ID NO 20
<211> LENGTH: 41
<212> TYPE: RNA
<213> ORGANISM: artificial
<220> FEATURE:
<223> OTHER INFORMATION: AMP responsive aptamer

<400> SEQUENCE: 20
uggguuggga agaaacugug gcacuucggu gccacaaccc u         41

<210> SEQ ID NO 21
<211> LENGTH: 29

```
<212> TYPE: RNA
<213> ORGANISM: artificial
<220> FEATURE:
<223> OTHER INFORMATION: Tobramycin responsive aptamer

<400> SEQUENCE: 21
uggcacgagg uuuagcuaca cucgugccu                                       29
```

STIMULUS-RESPONSIVE APTA CHELAMERS

CROSS-REFERENCE TO RELATED APPLICATIONS

This Non-Provisional Patent Application claims the benefit of U.S. Provisional Patent Application No. 61/080,214, filed on 11 Jul. 2008 and is a 371 National Phase of PCT/US2009/050217, filed on 10 Jul. 2009 and which is hereby incorporated by reference in its entirety.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON COMPACT DISC

The information recorded in electronic form submitted under Rule 13ter is identical to the sequence listing as contained in the international application as filed via EFS-Web. The subject matter of the sequence listing is incorporated herein by reference in its entirety.

BACKGROUND OF THE INVENTION

1. Field of the Invention

The present invention relates to the fields of chemistry and chemical and molecular biology, and to processes in which there is a direct or indirect qualitative or quantitative measurement or test of a material which contains at least one protein species. More particularly, the invention relates to subject matter in which a measurement or test utilizes at least one protein species in a specific binding protein or other specific ligand-receptor binding test or assay.

2. Description of Related Art

DNA-binding proteins (such as basic-region zippers, arc repressors, and type II restriction endonucleases) often harness dimer self-assembly (formation of protein-protein homo- or hetero-dimers) to recognize and bind with high affinity to their cognate duplex targets via bidentate interactions (K. S. Thompson, C. R. Vinson, E. Freire. *Biochemistry.* 1993, 32, 5491-5496; J. U. Bowie, R. T. Sauer. *Biochemistry.* 1989, 28, 7139-7143; and A. Pingoud, A. Jeltsch. *Nucleic Acids Res.* 2001, 29, 3705-3727, each of which is incorporated by reference herein in its entirety). In an elegant role reversal, the research groups of Hamilton and Neri, have independently developed synthetically modified DNA duplexes (which are not aptamers) that can bind to target proteins in a 2:1 fashion. For duplex DNA derived bidentate protein-binders see: S. Melkko, J. Scheuermann, C. E. Dumelin, D. Neri. *Nat. Biotechnol.* 2004, 22, 568-574; K. I. Sprint, D. M. Tagore, A. D. Hamilton, *Bioorg. Med. Chem. Lett.* 2005, 15, 3908-3911; S. Melkko, Y. Zhang, C. E. Dumelin, J. Scheuermann, D. Neri, *Angew. Chem. Int. Ed.* 2007, 46, 4671-4674; and J. Scheuermann, C. E. Dumelin, S. Melkko, Y. Zhang, L. Mannocci, M. Jaggi, J. Sobek, D. Neri, *Bioconjugate Chem.* 2008, 19, 778-785, each of which is incorporated by reference herein in its entirety. In particular, these researchers demonstrated that DNA duplex self-assembly results in the projection of synthetic protein-binding fragments in a bidentate manner (FIG. 3A), leading to the selective sequestration (via interaction with the synthetic protein-binding fragments) of a variety of proteins including carbonic anhydrase (Melkko, et al., *Nat. Biotechnol.* 2004), streptavidin (Sprint, et al., *Bioorg. Med. Chem. Lett.* 2005), trypsin (Melkko, et al., *Angew. Chem. Int. Ed.* 2007), and matrix metalloproteinase (Scheuermann, et al., *Bioconjugate Chem.* 2008). In addition, higher order intermolecular quadruplex based tetradentate protein-binders (FIG. 3B) have been recently introduced: D. M. Tagore, K. I. Sprint, S. Fletcher, J. Jayawickramarajah, A. D. Hamilton. *Angew. Chem. Int. Ed.* 2007, 46, 223-225, incorporated by reference herein in its entirety. In each of these systems, the chelate effect plays a central role in enhancing the affinity and selectivity of the multidentate binders above and beyond their individual monomeric components (which project only one synthetic protein-binding unit). See, e.g., S. Melkko, C. E. Dumelin, J. Scheuermann, D. Neri. *Chem. Biol.* 2006, 13, 225-231, incorporated by reference herein in its entirety. As used in this application, "chelate" and "chelation" refers to the caliper- or claw-like action of at least two functional groups which recognize and "grab" a target in at least two places. However, in each of the prior art systems described in FIGS. 3A and 3B, it is the synthetic protein-binding fragments that interact with protein targets, not the DNA fragments attached to the synthetic protein-binding fragments. Self-assembled oligonucleotides (ODNs) that form, say, a duplex or an intermolecular tetraplex as shown in FIGS. 3A and 3B, are not considered to be aptamers.

Aptamers are, generally, single stranded nucleic acids (DNA or RNA) that can fold into unique structures and bind to specific target molecules. As a result of their remarkable specificity and affinity, aptamers are currently pursued as tools for diagnostic applications. See: Hesselberth, J.; Robertson, M. P.; Jhaveri, S. D.; Ellington, A. D. "In vitro selection of nucleic acids for diagnostic applications" Rev. Mol. Biotechnol. 2000, 74, 15-25, incorporated by reference herein in its entirety. These same attributes also make aptamers viable pharmaceutical agents when they are selected against proteins implicated in human disease. See, e.g., Proske, D.; Blank, M.; Buhmann, R.; Resch, A. "Aptamers-basic research, drug development, and clinical applications" Appl. Microbiol. Biotechnol. 2005, 69, 367-374, incorporated by reference herein in its entirety. For instance, aptamers have been developed against various growth factors including the platelet derived growth factor (PDGF) and the vascular endothelial growth factor (VegF). Bell, C.; Lynam, E.; Landfair, D. J.; Janjic, N.; Wiles, M. N. "Oligonucleotide NX1838 inhibits VegF165-mediated cellular responses in vitro" In Vitro Cell. Dev. Biol. Anim. 1999, 35, 533-542; Floege, J.; Ostendorf, T.; Janssen, U.; Burg, M.; Radeke, H. H.; Vargeese, C.; Gill, S. C.; Green, L. S.; Janjic, N. "Novel approach to specific growth factor inhibition in vivo: antagonism of platelet-derived growth factor in glomerulonephritis by aptamers" Am. J. Pathol. 1999, 154, 169-179, each of which is incorporated by reference herein in its entirety. In fact, an anti-VegF aptamer (Macugen®) has been approved by the FDA for treatment of age-related macular degeneration and is currently commercialized.

In addition to the development of traditional aptamer systems that bind to molecules of interest, recent work has focused on aptamer conjugates that utilize aptamer-based binding characteristics to control the function of complex systems. Famulok, M.; Hartig, J. S.; Mayer, G. "Functional aptamers and aptazymes in biotechnology, diagnostics, and therapy" Chem. Rev. 2007, 107, 3715-3743, incorporated by reference herein in its entirety. An example of such an aptamer conjugate is shown in FIG. 1, which shows an allosteric aptamer linked to a ribozyme module (termed "aptazyme") to regulate ribozyme activity. See, e.g., Najafi-Shoushtari, S.; Famulok, M. "Competitive regulation of modular allosteric aptazymes by a small molecule and oligonucleotide effector" RNA 2005, 11, 1514-1520, incorporated by reference herein in its entirety. Aptamers can be combined with ribozymes to self-cleave in the presence of their target molecule. As shown in FIG. 1, two halves (labeled "A" and "B") of a hairpin ribozyme are tethered to a central flavin mononucleotide (FMN) binding aptamer (denoted by the wavy line between "A" and "B"). In the absence of FMN, the aptamer region remains unstructured (as represented by the wavy line), producing spatial separation of ribozyme domains A and B. Because the interaction of these two domains is critical for ribozyme activity (e.g., cleavage of the FMN-binding aptamer), the system remains in the "Inactive Form" in the absence of FMN. In marked contrast, addition of FMN leads to a conformational change in the aptamer moiety, via interaction between FMN and the FMN-aptamer, that brings domains A and B of the hairpin-ribozyme complex in close proximity. The conformational switch of the aptamer domain to a stem-loop structure upon binding to FMN, as shown in the "Active Form" on the right-hand side of FIG. 1, produces an activated aptazyme and leads to cleavage of the bound RNA at a specific site (denoted by the dashed arrow) with concomitant production of cleaved RNA substrate.

Another important aptamer system that has gained attention is the thrombin binding aptamer (Wu, Q.; Tsiang, M.; Sadler, J. E. "Localization of the single-stranded DNA binding site in the thrombin anion-binding exosite" J. Biol. Chem. 1992, 267, 24408-24412, incorporated by reference herein in its entirety), which undergoes a transition from a random coil to an intramolecular quadruplex upon binding to thrombin. Baldrich, E.; O'Sullivan, C. K. "Ability of thrombin to act as a molecular chaperone, inducing formation of quadruplex structure of thrombin-binding aptamer" Anal. Biochem. 2005, 341, 194-197, incorporated by reference herein in its entirety. Nucleic acids that are rich in guanine (e.g., the thrombin binding aptamer) are capable of forming four-stranded structures called quadruplexes (also known as G-quadruplexes, G-tetrads, or $G_4$-DNA). Quadruplexes contain guanine nucleotides arranged in a square (a tetrad, with the guanines denoting the corners of the square), and may be stabilized by monovalent cations (especially potassium ion, $K^+$) in the center of two tetrads or by binding to specific proteins (e.g., thrombin). Quadruplexes can be formed by DNA, RNA, LNA ("locked nucleic acid"), and PNA ("peptide nucleic acid"), and may be intramolecular (i.e., a solitary strand), bimolecular (i.e., two separate strands), or tetramolecular (i.e., four separate strands). Depending upon the strand orientation, or the orientation of the parts that form the quadruplex, quadruplexes may be described as parallel or antiparallel.

The complex comprising thrombin binding aptamer bound to thrombin protein is characterized by a dissociation constant ($K_d$) in the micromolar range, and inhibits thrombin activity (see, e.g., Pagano; B. Martino, L.; Randazzo, A.; Giancola, C. Biophysical Journal, 2008, 562-569, incorporated by reference herein in its entirety). Thrombin (also known as activated Factor II) is a serine protease that not only initiates blood coagulation (by catalyzing fibrin formation) but also acts as a general pro-inflammatory agent by interacting with protease-activated receptors (PARs) present on cell-surfaces. Cocks, T. M.; Moffatt, J. D. "Protease-activated receptors: sentries for inflammation?" Trends. Pharmacol. Sci. 2000, 21, 103-108, incorporated by reference herein in its entirety. In particular, thrombin activates PAR-1. Trypsin is another serine protease that can activate PARs (PAR-2, in particular) and, not surprisingly, is also associated with inflammatory conditions. In addition to being upregulated under inflammatory conditions, these two proteinases (i.e., thrombin and trypsin) have recently been implicated in tumor metastasis and invasion. Given the similarity in function of these two proteases and their critical activity in many salient diseases, much effort has been devoted to the development of broad-spectrum small-molecule chemical compounds that inhibit the activities of both thrombin and trypsin simultaneously. These efforts, though, have met with limited success. See, e.g., Bhattacharya, A.; Smith, G. F.; Cohen, M. L. "Effect of LY287045, a thrombin/trypsin inhibitor, on thrombin and trypsin-induced aortic contraction and relaxation" J. Pharmacol. Exp. Ther. 2001, 297, 573-581, incorporated by reference herein in its entirety. However, development of small-molecules that can selectively inhibit only thrombin and trypsin and not inhibit other members of the serine-protease family has been a significant challenge. Furthermore, prolonged inhibition of these two proteases can lead to serious side-effects including severe bleeding and death.

While the example described in FIG. 1 clearly illustrates the power of allosteric aptamers when tethered to catalytically active ODNs (oligonucleotides), there has been no prior exploration of the potential for developing allosteric aptamers tethered to synthetic, protein-binding, small molecules. Such a chimeric molecule (wherein aptamers are judiciously functionalized with synthetic, protein-binding, small-molecules with appropriate spacers) would provide for a modular and versatile system whose protein-binding activity is responsive to external stimuli. Further these newly conceived chimeric systems are expected to be a significant boon for novel technologies in diagnostics and therapeutics.

The technical problem underlying the present invention was therefore to overcome these prior art difficulties by: a) providing methods of preparing a novel class of molecules—termed herein "apta-chelamers"—that are well-controlled binders of selected target proteins; and b) preparing functional embodiments of said molecules. The solution to this technical problem is provided by the embodiments characterized in the claims.

BRIEF SUMMARY OF THE INVENTION

The present invention provides apta-chelamers comprising aptamer domains tethered to rationally designed synthetic protein-binding modules, and also provides methods of designing and making said apta-chelamers. Importantly, the present invention discloses that placement and identity of synthetic binding groups onto judiciously chosen allosteric aptamers leads to stimulus-responsive apta-chelamers that bind to target proteins through bidentate interactions.

In particular, the present invention discloses a "smart" apta-chelamer that (under specific conditions) is capable of simultaneously binding (and, thus, inhibiting) thrombin and trypsin. Furthermore, under a different set of specific conditions, the said apta-chelamer is capable of first binding to thrombin, which in turn, leads to substantially enhanced trypsin-binding. Conversely, under a third set of specific conditions the said aptamer is capable of first binding to trypsin, which in turn, leads to substantially enhanced thrombin-binding. Thus, apta-chelamers created according to the methods of this invention can be inactive (or significantly attenuated) in the absence of one of the binding partners (e.g., thrombin) and hence may serve as protective agents that are stimulated only upon disease inception. Importantly, the apta-chelamers of the present invention may be readily deactivated (or significantly attenuated) by providing oligonucleotides complementary to the core domain of the apta-chelamer strand. Thus, the dynamic system of this invention may be important for attenuating inflammatory processes (and cancer metastasis) where dual protease up-regulation is observed, while also enabling rapid antidote control if adverse side-effects are produced (e.g., due to overdose or bleeding caused by excess thrombin inhibition). Importantly, the present invention demonstrates the feasibility and generality of developing apta-chelamers that simultaneously or sequentially sequester two protein targets.

In view of the foregoing, the present invention discloses a compound of the formula:

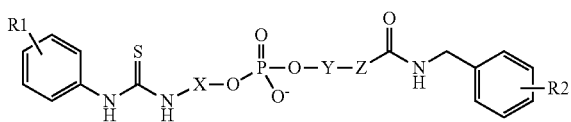

or a tautomeric form thereof, and/or a pharmaceutically acceptable salt thereof, and/or a pharmaceutically acceptable solvate thereof, wherein: R1 represents F, Br, Cl, or I; R2 represents acetamidine (—C(=NH)NH$_2$); X represents —(CH$_2$)$_{n1}$—, wherein n1 represents an integer in the range of from 3 to 15; Y represents an aptamer sequence; and Z represents —(CH$_2$)$_{n2}$—, wherein n2 represents an integer in the range of from 3 to 15.

R1 of said compound is preferably in the meta position, and R2 is preferably in the para position, n1 is preferably equal to 6, n2 is preferably equal to 9, and Y preferably comprises the nucleic acid sequence set forth in SEQ ID NO:6. More preferably, Y comprises the nucleic acid sequence set forth in SEQ ID NO:1. At least as preferably, Y comprises the nucleic acid sequence set forth in SEQ ID NO:4.

The present invention also discloses a compound of the formula:

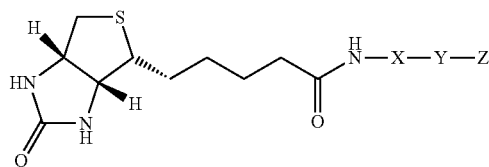

or a tautomeric form thereof, and/or a pharmaceutically acceptable salt thereof, and/or a pharmaceutically acceptable solvate thereof, wherein: X represents —(CH$_2$)$_{n1}$—, wherein n1 represents an integer in the range of from 3 to 15; Y represents an aptamer sequence; and Z represents —OH, —N$_3$, or the formula

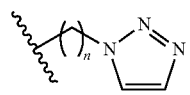

wherein n represents an integer in the range of from 1 to 6.

With said compound, n1 is preferably equal to 6, Y preferably comprises the nucleic acid sequence set forth in SEQ ID NO:10, and Z is N$_3$. More preferably, n1 is equal to 6, Y comprises the nucleic acid sequence set forth in SEQ ID NO:10, Z is the formula

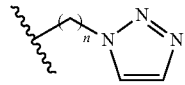

and n is equal to 6.

The present invention also discloses a compound of the formula:

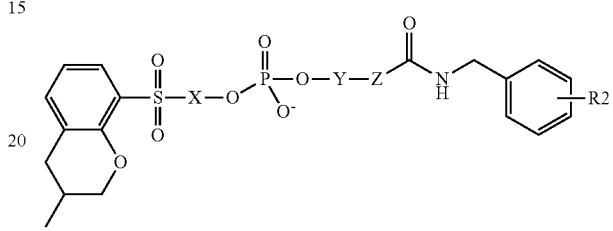

or a tautomeric form thereof, and/or a pharmaceutically acceptable salt thereof, and/or a pharmaceutically acceptable solvate thereof, wherein: R2 represents acetamidine (—C(=NH)NH$_2$); X represents —(CH$_2$)$_{n1}$—, wherein n1 represents an integer in the range of from 3 to 15; Y represents an aptamer sequence; and Z represents —(CH$_2$)$_{n2}$—, wherein n2 represents an integer in the range of from 3 to 15.

With said compound, n1 is preferably equal to 6, n2 is preferably equal to 9, and Y preferably comprises the nucleic acid sequence set forth in SEQ ID NO:6.

The present invention also discloses a compound of the formula:

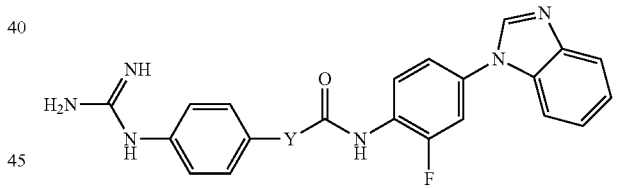

or a tautomeric form thereof, and/or a pharmaceutically acceptable salt thereof, and/or a pharmaceutically acceptable solvate thereof, wherein: Y preferably comprises the nucleic acid sequence set forth in SEQ ID NO:11.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements.

FIG. 3 shows prior art chimeric (non-aptamer) oligonucleotides. FIG. 3A shows the directed projection of bidentate protein-binding fragments (arrowheads) on a self-assembled DNA double helix. FIG. 3B shows a tetradentate projection of protein-binding fragments (arrowheads) on an intermolecular quadruplex scaffold. The circles containing "G" represent guanines, and the squares between the guanines denote guanine quartets.

FIG. 4 shows an apta-chelamer of the present invention, which binds to hemin. Here the hemin-binding aptamer is used as the core aptamer-domain, said core being tethered to synthetic protein-binding domains (arrowheads) at its 5' and 3' ends, in complex with hemin, $K^+$, and a target protein. Hemin has an iron (Fe) atom (not shown) in the center of the macrocycle, and a chloride counter anion (also not shown). The circles containing "G" represent guanines, and the squares between the guanines denote guanine quartets. Linker moieties (dashed lines) are interposed between and attached to the protein-binding domains (arrowheads) and the hemin-binding aptamer 5' and 3' ends. The macromolecular complex functions similarly to horseradish peroxidase in that it can catalyze oxidation of ABTS in the presence of $H_2O_2$, producing a colorimetric substrate ($ABTS^+$, or $ABTS_{ox}$).

FIG. 5 shows prior art bidentate molecules with the capacity to bind proteases. FIG. 5A shows a dimer of phenylguanidinium. FIG. 5B shows dibasic 3-aminomethyl benzenesulfonyl inhibitors attached to a rigid β-cyclodextrin core (represented by the truncated cone), the core having an external diameter of about 13 Å. FIG. 5C shows a heterobifunctional molecule incorporating benzamidine and iodophenylthiourea moieties.

FIG. 6 shows three different stimulus-responsive protein-binding apta-chelamers. The circles containing "G" represent guanines, and the squares between the guanines denote guanine quartets. When activated by thrombin, the apta-chelamers of FIGS. 6A and 6B are designed to inhibit tryptase and trypsin (while also inhibiting thrombin), respectively. The apta-chelamer of FIG. 6C is designed to bind to the PPE protein of Tuberculosis species via formation of a four-helix bundle. Hemin has an iron (Fe) atom (not shown) in the center of the macrocycle, and a chloride counter anion (also not shown). The critical two-helix bundle of the PPE protein is shown in white, while the two-helix portion of the PE protein (black helices) is appended onto the ends of the apta-chelamer. The dashed lines linking the protein binding elements (black helices) to the DNA termini of the apta-chelamer are spacer molecules.

FIG. 28 is a schematic showing how aptamers (here, the hemin-binding aptamer of SEQ ID NO:9) tethered to a synthetic protein-binding element (here, biotin) can result in an AC (AC-X1; Formula 9) that can signal the presence of an immobilized target protein via recognizing and binding to said target protein, and subsequent oxidation of ABTS in the presence of $H_2O_2$. Hemin has an iron (Fe) atom (not shown) in the center of the macrocycle, and a chloride counter anion (also not shown).

FIG. 29 shows a thrombin responsive aptamer conjugated to two separate protein binding fragments (triangles) for recognition of thrombin. In the presence of thrombin, the apta-chelamer folds into an intramolecular quadruplex conformation that yields the activated thrombin aptamer complex and necessarily orients the 3'- and 5'-termini in a coordinated manner. The coordinated protein binding fragments (triangles) are then available to recognize and bind to an additional thrombin molecule.

FIG. 31 shows coagulation factor IXa responsive aptamer (SEQ ID NO:11) in a hairpin configuration, conjugated to two protein binding moieties. In the configuration shown, the apta-chelamer will bind to two molecules of thrombin (one via the aptamer moiety, and one via the coordinated protein-binding moieties).

DETAILED DESCRIPTION OF THE INVENTION

Figure 1:
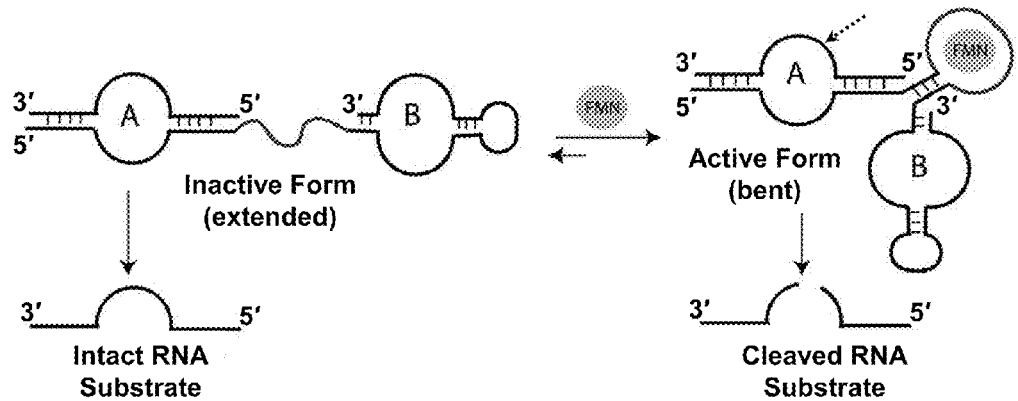
FIG. 1 shows a mechanism of aptamer controlled ribozyme activity. The upper left of FIG. 1 shows that ribozyme domains A and B are precluded from docking with one other because of the flexibility of the central aptamer moiety (depicted as a single wavy line between domains A and B). This leads to an inactive form of the ribozyme (extended conformation). The upper right of FIG. 1 shows conformational switching of the aptamer domain upon binding of the aptamer to flavin mononucleotide (FMN). This conformational switching results in the correct spatial placement of domains A and B (through a bent conformation), leading to activation of the ribozyme and cleavage of the RNA substrate at a specific site (dashed arrow).

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

DEFINITIONS

As is generally the case in biotechnology and chemistry, description of the present invention requires the use of a number of terms of art. Although it is not practical to do so exhaustively, definitions for some of these terms are provided here for ease of reference. Unless defined otherwise, all technical and scientific terms used herein have the same meaning as commonly understood by one of ordinary skill in the art to which the methods described herein belong. Definitions for other terms also appear elsewhere herein. However, the definitions provided here and elsewhere herein should always be considered in determining the intended scope and meaning of the defined terms. Other than in the operating examples or where otherwise indicated, all numbers or expressions referring to quantities of ingredients, reaction conditions, etcetera, used in the specification and claims are to be understood as modified in all instances by the term "about."

DNA molecules are said to have "5' ends" and "3' ends" because mononucleotides are joined in make oligonucleotides in a manner such that the 5' phosphate of one mononucleotide pentose ring is attached to the 3' oxygen of its neighbor in one direction, via a phosphodiester linkage. Therefore, an end of an oligonucleotide is referred to as the "5' end" if its 5'-phosphate is not linked to the 3' oxygen of a mononucleotide pentose ring. Alternatively, it is referred to as the "3' end" if its 3' oxygen is not linked to a 5' phosphate of a subsequent mononucleotide pentose ring. These ends are also referred to as "free" ends because they are not linked to upstream or downstream mononucleotides, respectively. Each strand of a double-stranded nucleic acid molecule may also be said to have 5'- and 3' ends, wherein the "5'" of any one of the paired strands refers to the end containing the accepted beginning of the particular region, gene, or structure, and the "3'" refers to the end downstream of the 5' end of that same strand. A nucleic acid sequence, even if internal to a larger oligonucleotide, may also be said to have 5' and 3' ends, although these ends are not free ends. In such a case, the 5' and 3' ends of the internal nucleic acid sequence refer to the 5' and 3' ends that said fragment would have were it isolated from the larger oligonucleotide. In either a linear or circular DNA molecule, discrete elements may be referred to as being "upstream" or 5' of the "downstream" or 3' elements. Ends are said to be "compatible" if: a) they are both blunt or contain complementary single strand extensions (such as that created after digestion with a restriction endonuclease); and b) at least one of the ends contains a 5' phosphate group. Compatible ends are therefore capable of being ligated by a double stranded DNA ligase (e.g., T4 DNA ligase) under standard conditions. Nevertheless, blunt ends may also be ligated.

By "aptamer" is meant a single-stranded DNA or RNA molecule that can form a defined three-dimensional structure, the shape of which allows for recognition and binding to a specific molecular target. Targets can be nearly any class of molecules including proteins, small-molecules, and even other nucleic acids.

By "apta-chelamer" or "AC" is meant a chimeric molecule comprising at least one aptamer moiety covalently bonded to at least one synthetic functional group. Optionally, the apta-chelamer may further comprise at least one spacer moiety covalently bonded to—and situated between—the aptamer moiety and the at least one synthetic functional group.

The terms "chelate," "chelation" and "bidentate" refer to the caliper- or claw-like action of at least two coordinated functional groups which recognize and "grab" a target in at least two places. Such actions are called chelate interactions or bidentate interactions, and a complex that contains a chelating ligand is called a chelate.

By "covalently bonded" is meant that two molecules (e.g., an aptamer and a synthetic functional group) are joined by covalent bonds, directly or indirectly. For example, a "covalently bonded" aptamer and synthetic functional group in an apta-chelamer may be immediately contiguous, or they may be separated by stretches of one or more spacers within the same chimera (i.e., the spacer would lie between the aptamer and the synthetic functional group).

The term "electrophoresis" refers to the use of electrical fields to separate charged biomolecules such as DNA, RNA, and proteins. DNA and RNA carry a net negative charge because of the numerous phosphate groups in their structure. Proteins carry a charge that changes with pH, but becomes negative in the presence of certain chemical detergents. In the process of "gel electrophoresis," biomolecules are put into wells of a solid matrix typically made of an inert porous substance such as agarose. When this gel is placed into a bath and an electrical charge applied across the gel, the biomolecules migrate and separate according to size, in proportion to the amount of charge they carry. The biomolecules can be stained for viewing via various standard methods (e.g., with ethidium bromide or with Coomassie dye) and isolated and purified from the gels for further analysis. Electrophoresis can be used to isolate pure biomolecules from a mixture, or to analyze biomolecules (such as for DNA sequencing).

By "fluorophore" is meant a component of a molecule that under certain conditions emits fluorescent light.

The terms "interact" and "interacting" are meant to include detectable interactions between molecules, and are intended to include apta-chelamer interactions with proteins, detectable by the methods of the present invention.

By "nucleotide" is meant a monomeric structural unit of nucleic acid (e.g., a DNA or RNA mononucleotide) consisting of a sugar moiety (a pentose: ribose, or deoxyribose), a phosphate group, and a nitrogenous heterocyclic base. The base is linked to the sugar moiety via a glycosidic bond (at the 1' carbon of the pentose ring) and the combination of base and sugar is called a nucleoside. When the nucleoside contains a phosphate group bonded to the 3' or 5' position of the pentose, it is referred to as a nucleotide. When the nucleotide contains one such phosphate group, it is referred to as a nucleotide monophosphate; with the addition of two or three such phosphate groups, it is called a nucleotide diphosphate or triphosphate, respectively. The most common, nucleotide bases are derivatives of purine or pyrimidine, with the most common purines being adenine and guanine, and the most common pyrimidines being thymidine, uracil, and cytosine. A sequence of operatively linked nucleotides is typically referred to herein as a "DNA sequence" or "oligonucleotide sequence" or "aptamer sequence," and unless otherwise indicated is represented herein by a formula whose left-to-right orientation is in the conventional direction of 5'-terminus to 3'-terminus.

As used herein, the term "oligonucleotide," refers to a short length of single-stranded polynucleotide chain. Oligonucleotides are typically less than 100 residues long (e.g., between 15 and 50), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

By "operably linked" is meant that aptamer sequences and synthetic protein-binding modules are placed into a functional relationship with one another. For example, an aptamer is operably linked to a synthetic protein-binding module if the aptamer and synthetic protein-binding module are covalently bonded. As a further example, an aptamer is operably linked to a synthetic protein-binding module if the aptamer and synthetic protein-binding module are each covalently bonded to a spacer element juxtaposed between the aptamer and the synthetic protein-binding module. Generally, "operably linked" means that an aptamer and at least one synthetic protein-binding module are connected in such a way as to permit reorientation of the at least one synthetic protein-binding module upon the aptamer moiety's binding to a target protein or other cognate molecule.

By "protein" or "polypeptide" is meant a sequence of amino acids of any length, constituting all or a part of a naturally-occurring polypeptide or peptide, or constituting a non-naturally occurring polypeptide or peptide (e.g., a randomly generated peptide sequence or one of an intentionally designed collection of peptide sequences).

By "target protein" is meant a peptide, protein, or domain of a protein whose function (i.e., whose ability to interact with an apta-chelamer) is being characterized with the methods of the invention. A target protein may further comprise an epitope tag, and so exist as a fusion protein.

Such a target protein, fusion protein, or target fusion protein may also be "immobilized" on a solid support (e.g., agarose or Sepharose®), which means that the fusion protein has been purified or isolated by affinity chromatography, using a solid support that has attached to it a moiety (e.g., glutathione) with affinity for the epitope tag (e.g., a GST epitope tag).

Since bidentate interactions can dramatically enhance protein-binding, we reasoned that development of a system where the projection of the two protein-binding fragments can be readily modulated (e.g., via addition of external stimuli) could result in "smart" agents with highly-controllable protein-binding activity. The present inventor achieved this aim by preparing a chimeric molecule, termed an "apta-chelamer" (AC) that exploits both the chelate (or "clawed") interactions of two synthetic fragments positioned in a directed orientation, with the structure-switching and molecular recognition properties of DNA aptamers. For important reviews on structure switching, functional, aptamers see: R. Nutiu, Y. Li. Chem. Eur. J. 2004, 10, 1868-1876; and M. Famulok, J. S. Hartig, G. Mayer. Chem. Rev. 2007, 107, 3715-3743, each of which is incorporated by reference herein in its entirety. Recently, researchers have combined two different aptamer domains tethered by a central ODN (oligonucleotide) linker unit to enhance target protein binding through bivalency (see: H. Hasegawa, K. Taira, K. Sode, K. Ikebukuro. Sensors, 2008, 8, 1090-1098; and Y. Kim, W. Tan. PNAS. 2008, 105, 5664-5669, incorporated by reference herein in its entirety.)

Figure 5A:
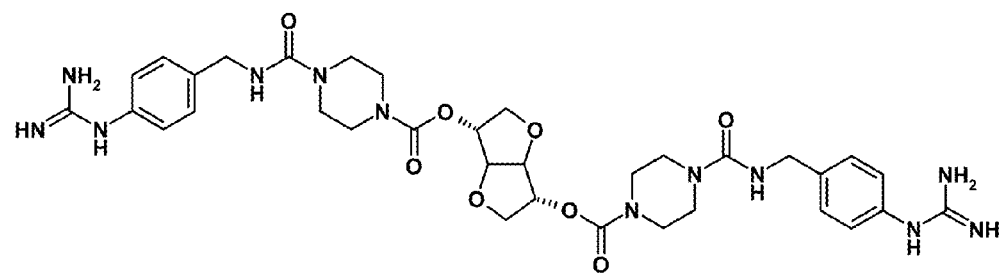
FIGS. 5A and 5B show tryptase inhibitors.
Figure 5B:
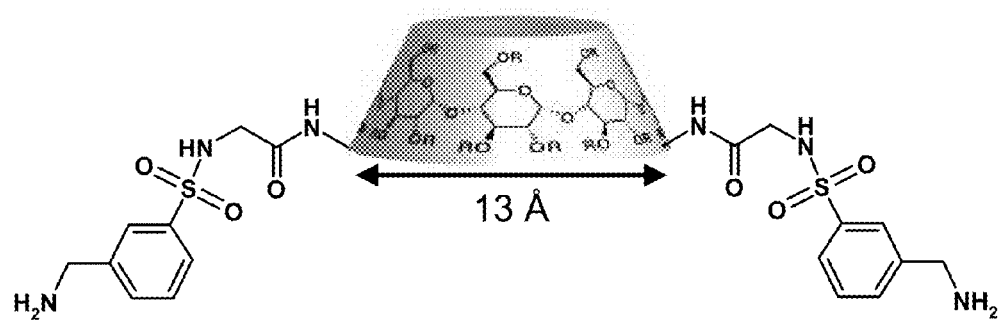

The identification of bivalent molecules capable of binding to important protein targets is an important component of this invention. One salient protein of interest is human β-tryptase, a serine protease implicated in inflammatory disorders such as asthma. Abraham, W. M. "Tryptase: potential role in airway inflammation and remodeling" Am. J. Physiol. Lung. Cell. Mol. Physiol. 2002, 282, 193-196. The crystal structure of human β-tryptase reveals a tetramer consisting of four identical active sites pointing toward a central pore. Sommerhoff, C. P.; Bode, W.; Pereira, P. J. B.; Stubbs, M. T.; Sturzebecher, J.; Piechottka, G. P.; Matschiner, G.; Bergner, A. "The structure of the human βII-tryptase: Fo(u)r better of worse" Proc. Natl. Acad. Sci. USA. 1999, 96, 10984-10991, incorporated by reference herein in its entirety. The distance between two nearest neighboring active sites is 33 Å. Various bidentate molecules containing arginine mimics, such as dimers of phenylguanidinium (see, e.g., FIG. 5A, and Selwood, T.; Elrod, K. C.; Schechter, N. M. "Potent bivalent inhibition of human tryptase-β by a synthetic inhibitor" Biol. Chem. 2003, 384, 1605-1611, incorporated by reference herein in its entirety), and m-aminomethylphenylalanine motifs (see, e.g., Schaschke, N.; Dominik, A.; Matschiner, G.; Sommerhoff, C. P. "Bivalent inhibition of β-tryptase: Distance scan of neighboring subunits by dibasic inhibitors" Bioorg. Med. Chem. Lett. 2002, 12, 985-988, incorporated by reference herein in its entirety) have been shown to bind effectively to these two distinct sites when attached to appropriate scaffolds. Furthermore, Schaschke et al. have demonstrated that dibasic 3-(aminomethyl)benzenesulfonyl inhibitors fastened to a rigid β-cyclodextrin core (see, e.g., FIG. 5B), with an external diameter of 13 Å, can fit inside the central pore and project the tryptase binding units for optimal inhibition. Schaschke, N.; Matschiner, G.; Zettl, F.; Marquardt, U.; Bergner, A.; Bode, W.; Sommerhoff, C. P.; Moroder, L. "Bivalent inhibition of human β-tryptase" Chem. Biol. 2001, 8, 313-327, incorporated by reference herein in its entirety.

Figure 11:
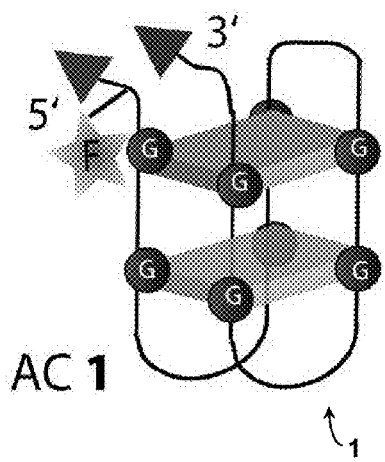
FIG. 11 shows schematically the intramolecular quadruplex formed by apta-chelamer 1 ("AC 1") upon incubation with high concentrations of potassium cations ($K^+$) resulting in the pre-organized projection of two synthetic protein-binding arms. The circles containing "G" represent guanines, and the squares between the guanines denote guanine quartets. The star containing "F" represents an optional fluorescein moiety. The fluorescein moiety need not be present, or may be replaced with a different fluorophore, chromophore, or other detectable label.
Figure 15:
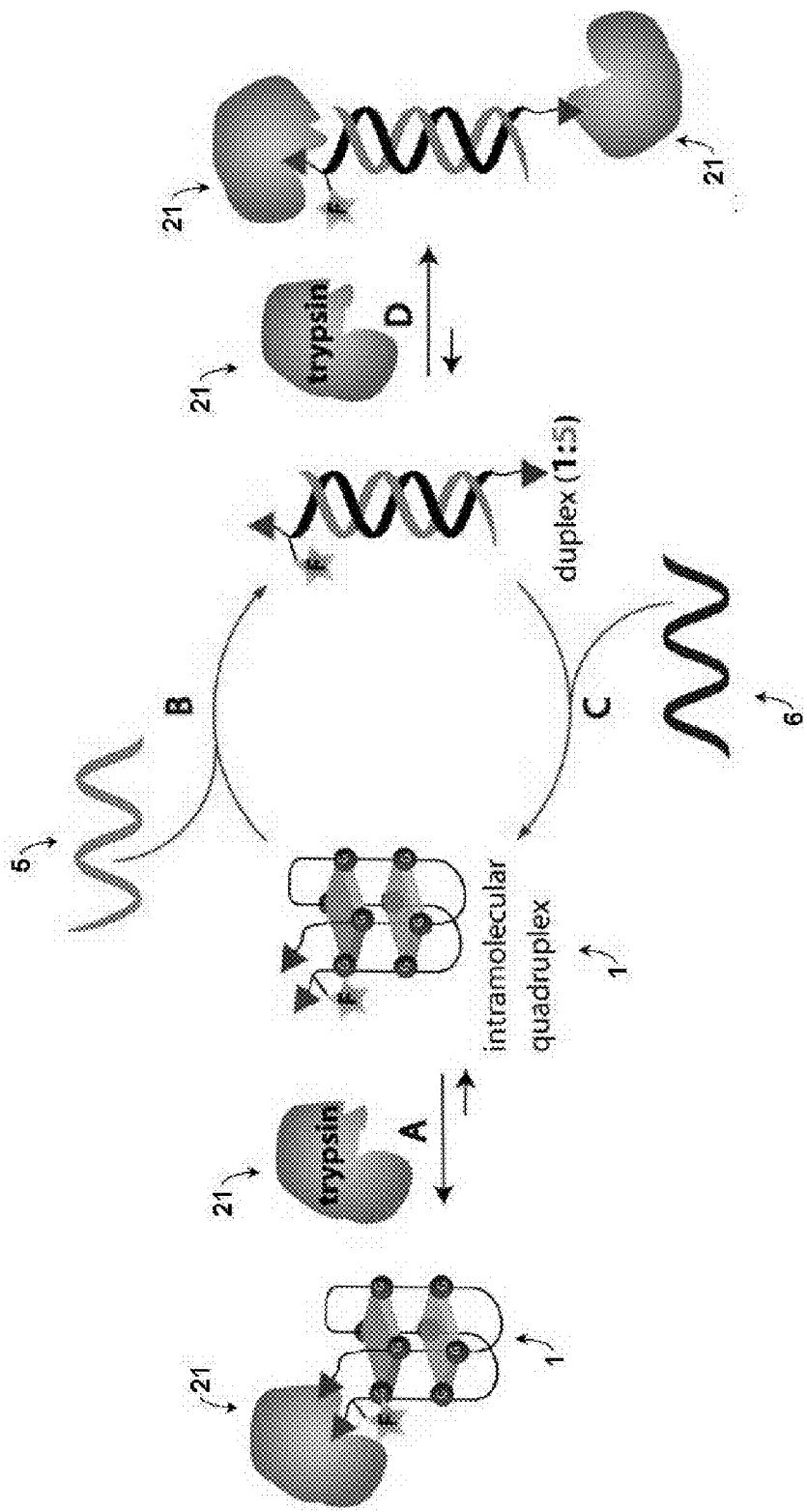
FIG. 15 shows how AC 1 can be cycled from the intramolecular quadruplex conformation to the duplex conformation, and vice-versa, through sequential incubation with stimulus-oligonucleotides. As shown along pathway A, the intramolecular quadruplex conformation of AC 1 results in strongly-favored bidentate binding to trypsin. Along pathway B, incubation of AC 1 in the presence of a complementary sequence leads to the formation of a duplex between AC 1 and ODN 5 (SEQ ID NO:2, complementary to the core domain of AC 1), where the ba and ipt-arms of AC 1 are projected in opposite directions (duplex 1:5). Along pathway C, incubation of the duplex 1:5 conformation with excess ODN 6 (SEQ ID NO:3, composed of the same sequence as the core domain of AC 1, but with 5'-OH, not $PO_4$) results in the predominant formation of a duplex between ODN 6 and ODN 5 (duplex 5:6, not shown), and single-stranded AC 1 intramolecular quadruplex. Along pathway D, if the duplex 1:5 is incubated in the presence of trypsin (21), diminished trypsin-binding results because only one binding arm of AC 1 interacts with each molecule of trypsin.

With the instant disclosure, the present inventor details the preparation, folding characteristics, and highly versatile trypsin-binding ability of AC 1 (see: Formula 3; also referred to as ODN 1). Specifically demonstrated is that the conformation of AC 1 can be cycled from an intramolecular quadruplex (FIGS. 11, 15) to a duplex and vice-versa through sequential incubation with stimulus-oligonucleotides. Note that the terminal dT (thymine deoxynucleotide) on the 5'-end is attached to fluorescein (star). This optional fluorescein moiety endows AC 1 with the capacity to be analyzed by fluorescence polarization or by FRET (fluorescence resonance energy transfer). A variety of different fluorophores can be utilized in lieu of fluorescein (e.g., rhodamine, Alexa Fluor dyes, etc.). In addition, the 3'-terminus can also be functionalized with an appropriate photoactive molecule (e.g., a quencher molecule) that can interact (via electron or energy transfer) with the 5'-fluor end. Importantly, this structure-switching mechanism leads to the projection of bidentate or monodentate trypsin-binding arms, respectively (FIG. 15).

Subsequent incubation of these two distinct conformations with trypsin results in dramatically altered binding activity. Such stimuli responsive systems are envisioned to be important in generating "smart" therapeutics whose activity can be modulated (i.e., enhanced or attenuated) through addition of external inputs.

Figure 2:
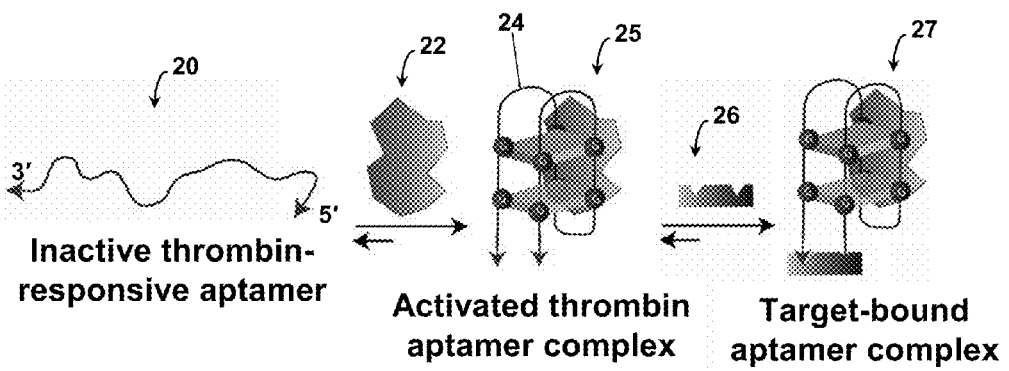
FIG. 2 is a schematic diagram demonstrating the function of chimeric aptamers of the present invention. In the absence of high concentrations of templating potassium cations (or known proteins that bind to the apta-chelamer), the apta-chelamer is predominantly in a random-coil conformation (structure to the left). In the presence of thrombin the apta-chelamer folds into an intramolecular quadruplex conformation that yields the activated thrombin aptamer complex and necessarily orients the 3'- and 5'-termini in a directed manner. The circles containing "G" represent guanines, and the squares between the guanines denote guanine quartets. This structural-switch thereby preorganizes the arms of apta-chelamer to undergo bidentate interactions with trypsin, resulting in a target-bound aptamer complex. Importantly, bidentate interactions will greatly enhance binding of the apta-chelamer to trypsin.

An exemplary schematic for producing apta-chelamers of the present invention is shown in FIG. 2. Briefly, the thrombin responsive aptamer of SEQ ID NO:1 (20) is flanked at its 5' and 3' termini by synthetic protein binding domains (represented by arrowheads at the 5' and 3' termini of (20)), to yield an inactive thrombin-responsive aptamer. In the absence of its stimulus molecule (e.g., thrombin (22)), the aptamer chimera remains in a random coil conformation and the synthetic protein binding domains are not held in any pre-organized manner. Upon association with the stimulus molecule (22), the aptamer chimera undergoes a conformational switch (assembling an intramolecular quadruplex (24), and yielding an activated thrombin aptamer complex (25)) that positions the 5' and 3' ends parallel to one another, and consequently arranges the attached synthetic binding elements into a well-defined and predetermined conformation. This conformational activation step enables strong bidentate interactions (via the chelate effect) between the newly organized synthetic binding elements and a target protein (26) containing binding sites complementary to the arrangement of the synthetic binding elements, yielding the target-bound aptamer complex (27).

The prediction and selection of synthetic elements useful for binding to a particular protein according to the methods of the present invention may be based partly upon literature precedence. For example, a number of bivalent small molecules against various proteins (including p38 kinase, urokinase, tryptase, c-SRC, and PTP1B) are known. See, e.g., Rees, D. C.; Congreve, M.; Murray, C. W.; Carr, R. "Fragment-based lead discovery" Nat. Rev. Drug Discovery. 2004, 3, 660-672, incorporated by reference herein in its entirety. Functional systems according to the methods of the present invention may thus incorporate each respective half of such bivalent molecules onto the 5' and 3' termini of apta-chelamers. Attachment of these binding modules to aptamers may be achieved through a combination of established technologies (see, e.g., Manoharan, M. "Oligonucleotide conjugates as potential antisense drugs with improved uptake, biodistribution, targeted delivery, and mechanism of action" Antisense & Nucleic Acid Drug Development, 2002, 12, 103-128; and Bioconjugate Techniques by Greg T. Hermanson, Elsevier Science, USA, each of which is incorporated by reference herein in its entirety) and via novel synthetic procedures disclosed herein.

Figure 32:
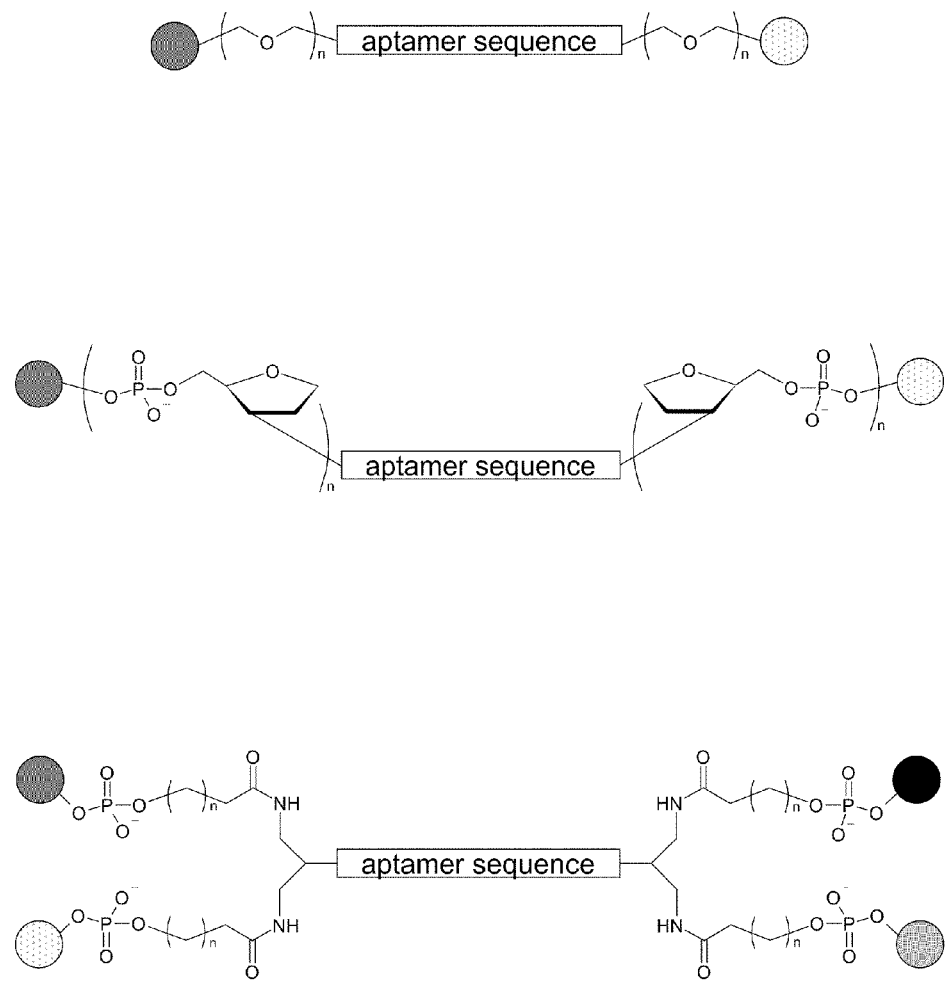
FIG. 32 shows additional examples of spacer structures which may be placed between the aptamer termini of any chosen aptamer sequence (boxes) and the protein binding groups (represented by circles), depending upon (for example) the distances required to span between binding sites on a chosen protein. As will be appreciated by those of ordinary skill in the art, the aptamer sequences may be modified to bear fluorometric or colorimetric moieties.

The mere identification of potential binding modules, though, is insufficient to ensure that a given aptamer with known characteristics will behave as desired when said binding modules are attached to the aptamer 5' and 3' ends. In fact, the spacer type and length are of special importance. For instance, the spacers should be of appropriate length to allow for the ligation of both binding fragments without generating any negative energetic strains. Further the rigidity of the spacer can have a dramatic influence on the sampling of conformational space available to the binding groups (see, e.g., Whitesides at al. J. Am. Chem. Soc. 2007, 129, 1312-1320; Ungaro et al. Chem. Soc. Rev. 2007, 36, 254-266, each of which is incorporated by reference herein in its entirety). Thus, carefully chosen spacer units are placed between the aptamer termini and the protein binding groups, depending on—for example—the requisite distance that needs to spanned to access both binding sites on a particular protein, but depending ultimately upon empirical data obtained from tests of apta-chelamers with different spacer units. Importantly, a variety of spacer units with differing lengths (e.g., C3 through C12), hydrophobicities (e.g., alkyl, oligoethylene glycol, polyethylene glycol), and rigidities (e.g., abasic deoxyribose) are commercially available as phosphoramidite monomers (Glen Research Corporation, Sterling, Va.). Thus, such spacers may be incorporated into oligonucleotide sequences relatively easily, and apta-chelamers incorporating different spacers may be synthesized (without undue experimentation) to meet predicted or suspected requirements (FIG. 32).

An important requisite for the present invention is that the protein binding elements, when conjugated to the oligonucleotide scaffold, must be effective in binding to the targeted protein through chelate interactions. Further, the bidentate interactions should be significantly more favorable than monodentate interactions between any single protein binding element alone (i.e., the 5' side or the 3' side alone) and the targeted protein. Projection of bidentate synthetic protein binding motifs via a duplex (bimolecular) DNA scaffold (see, e.g., FIG. 3A) has been clearly demonstrated previously by Neri and coworkers (see also U.S. Patent Application Publication Numbers 2004/0014090 A1 and 2006/0154246 A1, incorporated by reference herein in its entirety). Neri and coworkers used small-molecule libraries appended to one end of single-stranded DNA oligonucleotides. The oligonucleotides formed double helical DNA with their complementary strands (also bearing small molecules), to generate bimolecular, bidentate binders for streptavidin, carbonic anhydrase, and human serum albumin. Dumelin, C. E.; Scheuermann, J.; Melkko, S.; Neri, D. "Selection of streptavidin binders from a DNA-encoded chemical library" Bioconj. Chem. 2006, 17, 366-370; Melkko, S.; Scheuermann, J.; Dumelin, C. E.; Neri, D. "Encoded self-assembling chemical libraries" Nat. Biotech. 2004, 22, 568-574. Furthermore, the present inventor played a key role in demonstrating that intermolecular quadruplexes (specifically, tetramolecular, parallel quadruplexes) appended with four synthetic protein binding elements (see, e.g., FIG. 3B) can selectively bind and denature cytochrome C (cyt C). Tagore, D. M.; Sprint, K. I.; Fletcher, S.; Jayawickramarajah, J.; Hamilton, A. D. "Protein recognition and denaturation by self-assembling fragments on a quadruplex scaffold" Angew. Chem. Int. Ed. 2007, 46, 223-225, incorporated by reference herein in its entirety. The parallel quadruplexes were functionalized with specifically designed anionic and hydrophobic modules that bind to a central hydrophobic patch on cytochrome C (cyt c) flanked by lysine residues. Importantly, the single stranded (i.e., monodentate) control is not capable of denaturing cyt C. Taken together, the prior art demonstrates that self-assembled double-stranded oligonucleotide scaffolds enable the coordinated projection of synthetic protein binding elements, and that multivalent interactions are important in enhancing target protein sequestration. The prior art fails to teach, though, that a single-stranded oligonucleotide scaffold—an aptamer—may bind to a cognate target and provide precisely coordinated projection of multiple synthetic binding elements.

The development of stimulus-responsive apta-chelamers, which bind to target molecules via chelate interactions only upon prior activation, is interesting and useful because such allosteric aptamers can serve as models of more complex allosteric proteins (see, e.g., Gunasekaran, K.; Ma, B.; Nussinov, R. "Is allostery an intrinsic property of all dynamic proteins?" Proteins: Structure, Function, and Bioinformatics 2004, 57, 433-443, incorporated by reference herein in its entirety). In addition, it is expected that apta-chelamers developed according to the methods of the present invention will have importance in both therapeutic and diagnostic applications. Therapeutically, such chimeras may lead to controlled drugs with low toxicity as a result of an inbuilt mechanism—the complementary oligonucleotide, which may also be modified to enhance its effectiveness—for modulating the activity of the drug. Similarly, overdosing on such therapeutic agents will be extremely difficult because a) a stimulus molecule is necessary for activation and b) an antidote (i.e., the complementary strand of the aptamer) is readily available to inhibit aptamer activity. Furthermore, it is anticipated that such "smart" aptamers may lead to the development of drugs that can simultaneously block two pathways in a disease. An example of such an aptamer chimera is illustrated in this disclosure with the thrombin-stimulated tryptase-binding aptamer for inhibiting the pro-inflammatory activity of both thrombin and tryptase.

It is expected that apta-chelamers will also be important in diagnostic applications because a signaling agent can be used as a stimulus molecule. Hence, no laborious synthesis involving covalent attachment of chromophore or fluorophore labels is necessary. Thus a single self-assembled supramolecule can serve both as the protein binding and signaling agent. An example of such a complex is described herein with the hemin responsive aptamer. In contrast to such a multifunctional aptamer, the current gold standard in diagnostics—the antibody-based ELISA (enzyme-linked immunosorbent assay)—is time-consuming, laborious, and usually needs two sets of antibodies (i.e., a primary antibody directed to a particular antigen, and a secondary chromophore-conjugated antibody directed to the first antibody) for analyte detection. In addition, apta-chelamers produced according to the methods of the present invention possess the usual advantages of aptamer-based detection systems (including longer shelf-life, ease of preparation, and modulation of the kinetic parameters of binding). For a comparison of aptamer-versus-antibody diagnostics, see: Jayasena, S. D. "Aptamers: an emerging class of molecules that rival antibodies in diagnostics" Clin. Chem. 1999, 45, 1628-1650, incorporated by reference herein in its entirety.

The thrombin responsive aptamer, with "core" sequence 5'-GGTTGGTGTGGTTGG-3' (SEQ ID NO:6) and represented schematically in FIG. 2 as a random coil, is an example of a system that undergoes a clear transition from random coil to intramolecular quadruplex upon binding to thrombin (see, e.g., FIG. 2). Wu, Q.; Tsiang, M.; Sadler, J. E. "Localization of the single-stranded DNA binding site in the thrombin anion-binding exosite" J. Biol. Chem. 1992, 267, 24408-24412, incorporated by reference herein in its entirety. The resultant complex inhibits thrombin activity and is characterized by a dissociation constant (KO in the micromolar range. Furthermore, crystallographic studies have shown that the bound complex projects the 5'- and 3'-termini in a parallel orientation, with a separation of ~13 Å between termini. See, e.g., Padmanabhan, K., et al. J. Biol. Chem. 1993, incorporated by reference herein in its entirety. This aptamer sequence (SEQ ID NO:6) was modified and used as described herein to target proteins that bind divalent ligands through two distinct binding sites (e.g., a primary or "active" site and an exosite).

EXAMPLE 1

Design of Apta-Chelamers and of Trypsin-Binding Arms

Apta-chelamer 1 (FIG. 12, Formula 3) comprises a core aptamer domain derived from the thrombin-binding aptamer sequence (SEQ ID NO:6) and, as such, is capable of forming a chair-type intramolecular quadruplex in the presence of thrombin (see Q. Wu, M. Tsiang, J. E. Sadler, *J. Biol. Chem.* 1992, 267, 24408-24412; and E. Baldrich, C. K. O'Sullivan. *Anal. Biochem.* 2005, 341, 194-197, each of which is incorporated by reference herein in its entirety) or templating potassium cations (see S, Nagatoishi, Y. Tanaka, K. Tsumoto. *Biochem. Bioph. Res. Corn.* 2007, 352, 812-817, incorporated by reference herein in its entirety). In this AC, one deoxythymidine (dT) is added to the 3' end of SEQ ID NO:6, and two are added to the 5' end (FIG. 12, Formula 3), yielding SEQ ID NO:1. The terminal 5'-dT is functionalized with fluorescein. The fluorescein fluorophore serves as a spectroscopic marker to study trypsin-binding through fluorescence anisotropy titrations.

Figure 13:
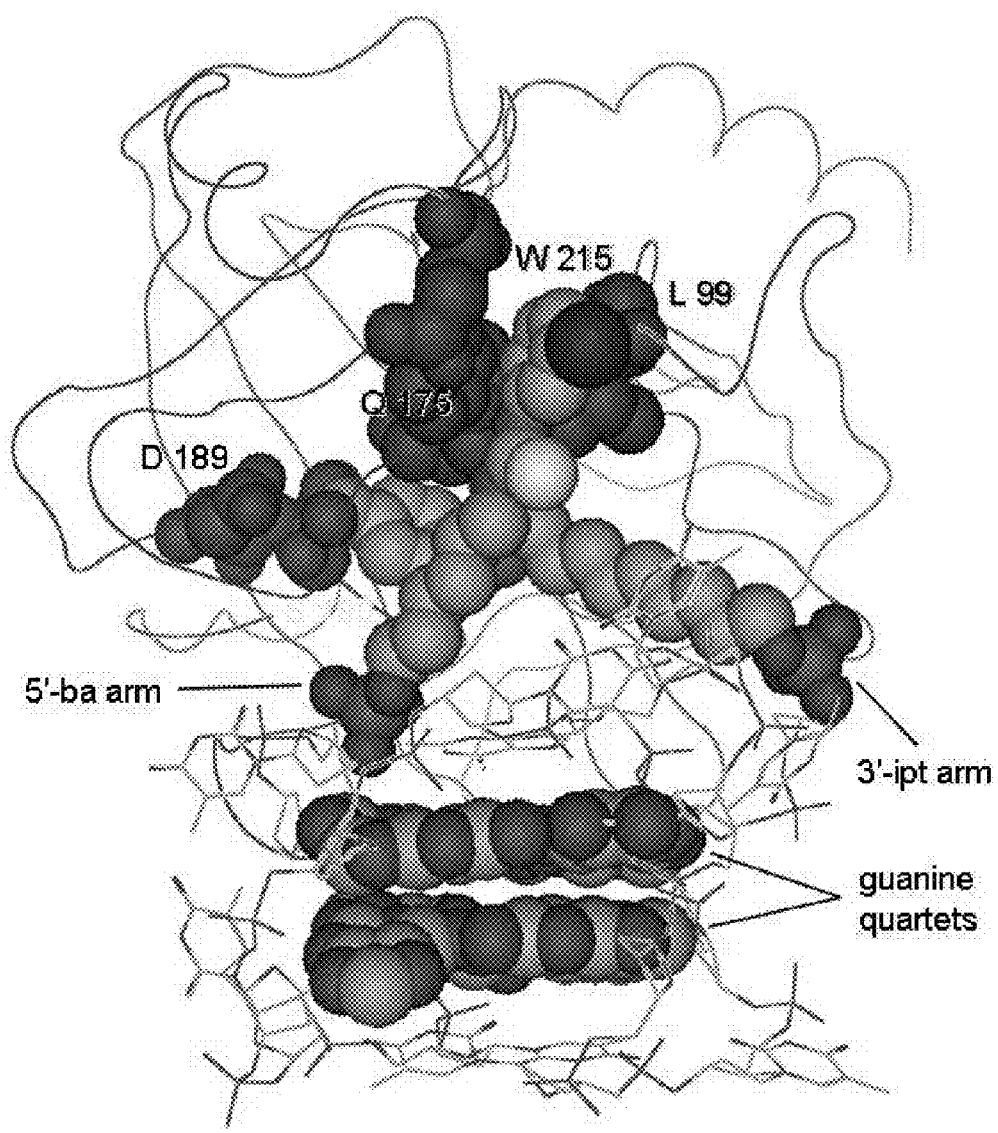
FIG. 13 Schematic illustrating possible bidentate interactions between the quadruplex form of AC 1 and bovine trypsin (shown in brown). The 5'-ba arm and 3'-ipt arm are bound to residues in the trypsin S1 and S4 pockets, respectively (key residues labeled D 189, Q 175, W 215, and L 99, using standard one-letter amino acid symbols). The two stacked guanine quartets formed by AC 1 are depicted as space-filling models. The model of 1 was derived from the x-ray structure of the thrombin-binding aptamer in the quadruplex conformation (PDB code: 1HUT). The model of trypsin was derived from the x-ray structure of bovine trypsin (PDB code: 1f0u). For the sake of clarity, the fluorescein moiety of AC 1 has been omitted.

The 5' and 3'-termini flanking the core domain are functionalized with spacers tethered to synthetic trypsin binding groups benzamidine (ba) and iodophenylthiourea (ipt), respectively. These fragments were chosen because benzamidine is a well-known active site (S1 pocket) inhibitor of trypsin, and the potency of ba can be dramatically increased by covalent attachment, via appropriate spacers, to aromatic hydrophobic elements (such as ipt) (R. T. Talhout, J. B. F. N. Engberts. *Eur. J. Biochem.* 2001, 268, 1554-1560; S. Maignan, J.-P. Guilloteau, S. Pouzieux, Y. M. Choi-Sledeski, M. R. Becker, S. I. Klein, W. R. Ewing, H. W. Pauls, A. P. Spada, V. Mikol. *J. Med. Chem.* 2000, 43, 3226-3232; and Melkko, et al., *Angew. Chem. Int. Ed.* 2007, each of which is incorporated by reference herein in its entirety). Literature precedence and preliminary modelling studies indicate that ipt potentially binds to the canonical exosite (S4 pocket) in a similar manner to other aromatic hydrophobic modules. Based on these putative trypsin-binding pockets (FIG. 13), C10 and C6 spacers were chosen as appropriate linkers.

The ba and ipt fragments have been demonstrated by others to inhibit trypsin (for example, the molecule of Formula 2) composed of both these fragments inhibits trypsin with an $IC_{50}$ of 98 nM. However, the nature of the exosite on trypsin that interacts with the ipt unit has not been shown. Thus, the present inventor searched for similar bifunctional molecules that bind bovine trypsin, finding a series of molecules that possess a benzamidine active site binder linked to a terminal hydrophobic moiety that serves as a canonical S4 site binder. In particular, a β-amino ester (Formula 1), which incorporates a ba moiety and an aminomethylbiphenyl unit has been crystallized with bovine trypsin. In addition, the distance between the ba fragment and the furthest hydrophobic module on Formula 1 is close to the distance between the ba and the benzene ring on the ipt unit of Formula 2 (as judged by modeling studies using MOE LigX; compare FIG. 25 with middle panel of FIG. 26). Thus, the present inventor hypothesized that ipt potentially binds to the S4 pocket on trypsin and hence a model was built (FIG. 13) with the required spacers (i.e. the linker molecules between the aptamer core domain of 1 and the synthetic binding fragments). This model was prepared using the MOE software and was minimized under an Amber99 forcefield (RMS gradient=0.05).

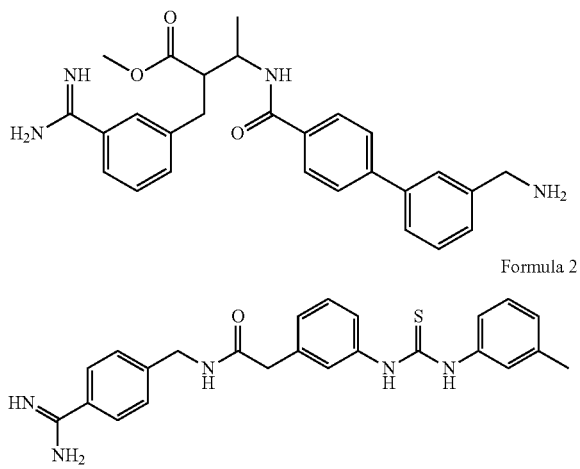

Formula 1

Formula 2

Figure 25:
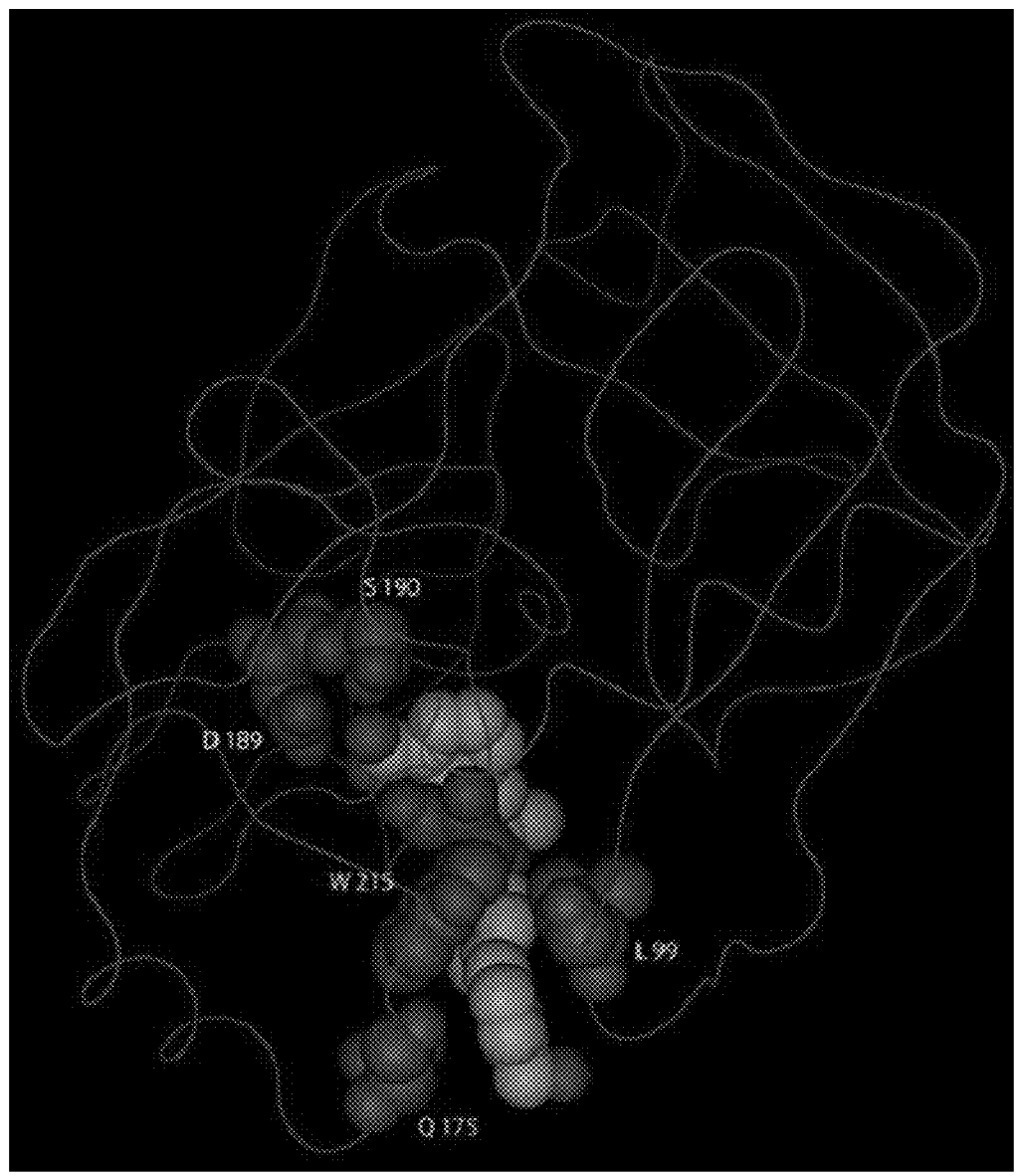
FIG. 25 shows an X-ray structure depicting the key interactions of Formula 1 with bovine trypsin.
Figure 26:
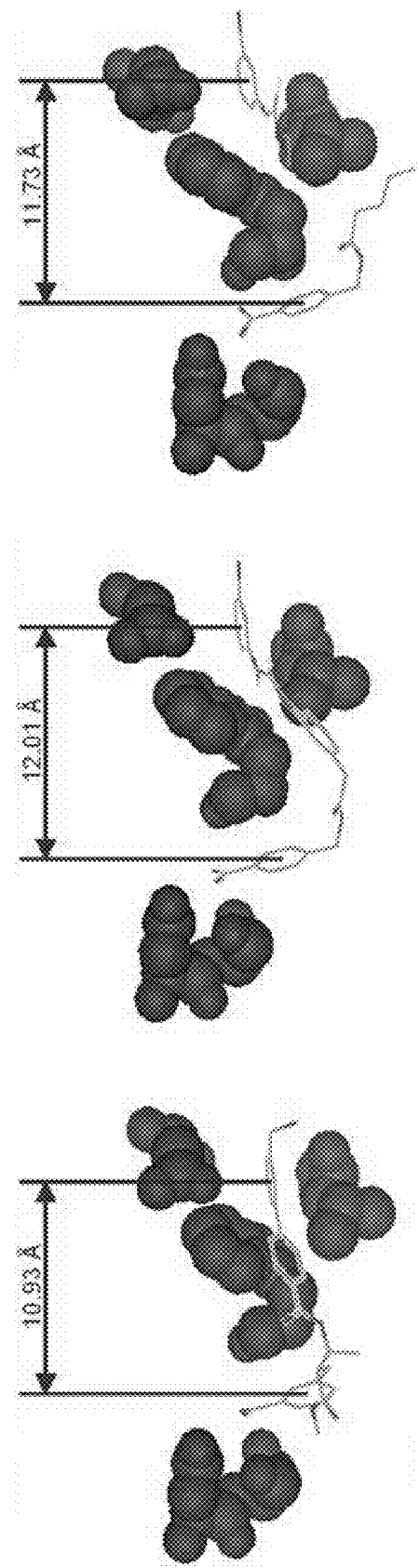
FIG. 26 shows a comparison of the computed bound structure of Formula 2 (middle) and the synthetic binding fragments of AC 1 (right) with the X-ray structure of Formula 1 (left).

For the sake of comparison, the X-ray structure of Formula 1 bound to trypsin is shown in FIG. 25. This structure reveals key interactions in the S1 and S4 pockets. In the S1 pocket, residues S190 and D189 are both involved in direct hydrogen bonding interactions with the amidine nitrogens. In the S4 pocket, residues W215, L99, and Q175 make van der Waals contacts with the biphenyl group of compound Formula 1.

EXAMPLE 2

Apta-Chelamer Preparation

Figure 7:
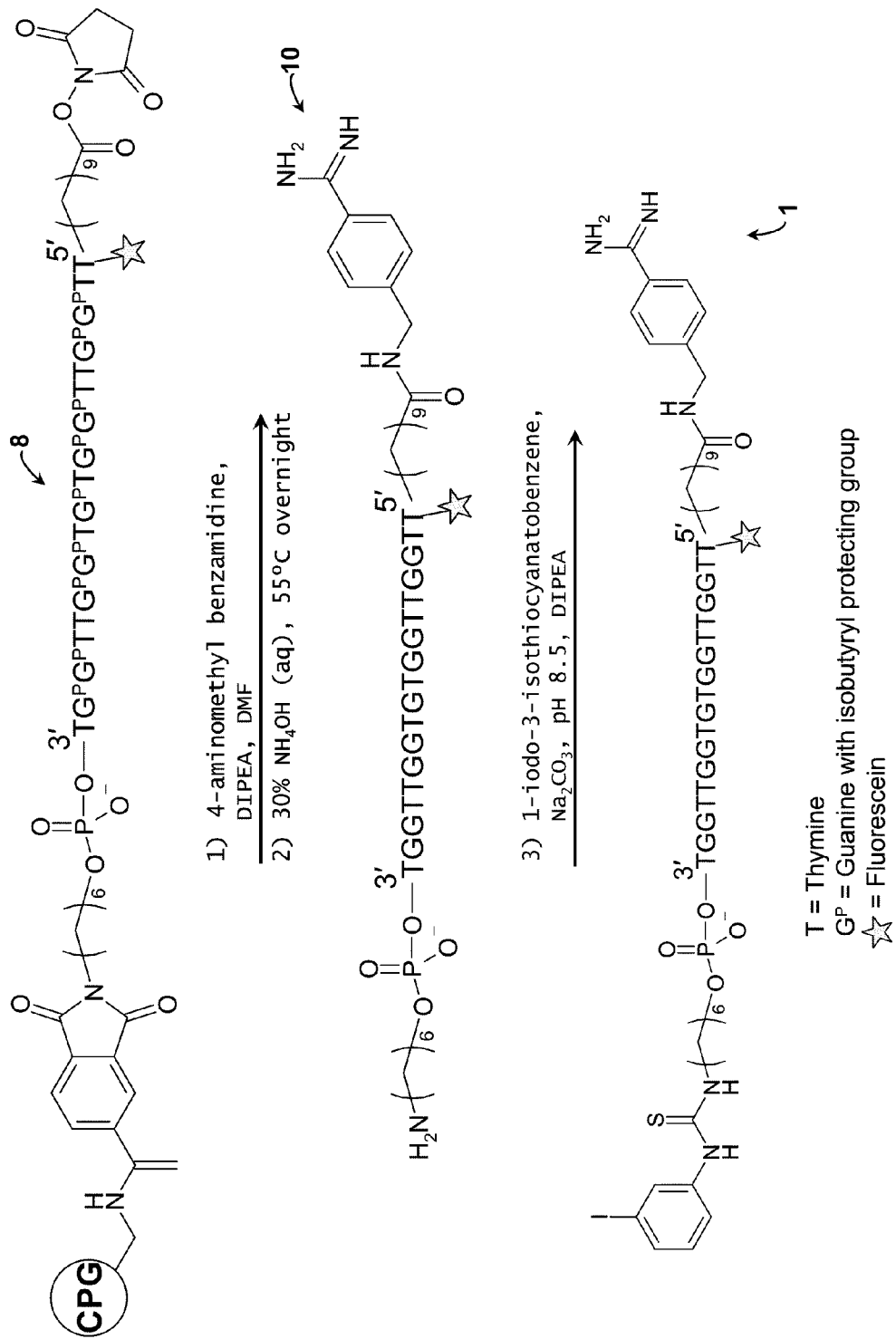
FIG. 7 is a schematic diagram of the steps for synthesizing the thrombin-responsive trypsin-binding apta-chelamer of the present invention (AC 1). AC 1 was prepared by a simple two-step procedure. Briefly, the core aptamer sequence bearing a C10 spacer tethered to an N-hydroxysuccinimidyl ester on the 5'-terminus (8; alternatively, "ODN 8") and a C6 spacer linked to a phthalimide protected amine on the 3'-terminus (which is attached to a controlled pore glass bead) was reacted with 4-aminomethyl benzamidine under basic conditions. The crude 5'-reacted product was cleaved off the bead and globally deprotected using aqueous ammonium hydroxide, affording compound (10; alternatively, "ODN 10"), which contains a free amine terminus on the 3' end along with a C6 spacer. The deprotection step also served to cleave the phthalimide protecting group on the 3'-terminus. Reaction of compound (10) under basic conditions with 1-iodo-3-isothiocyanatobenzene (3-iodophenylisothiocyanate) yields apta-chelamer 1 (1), termed "AC 1," or sometimes "ODN 1," which is identical to Formula 3 below. The fluorescein moiety (star) need not be present, or may be replaced with a different fluorophore, chromophore, or other detectable label.
Figure 8:
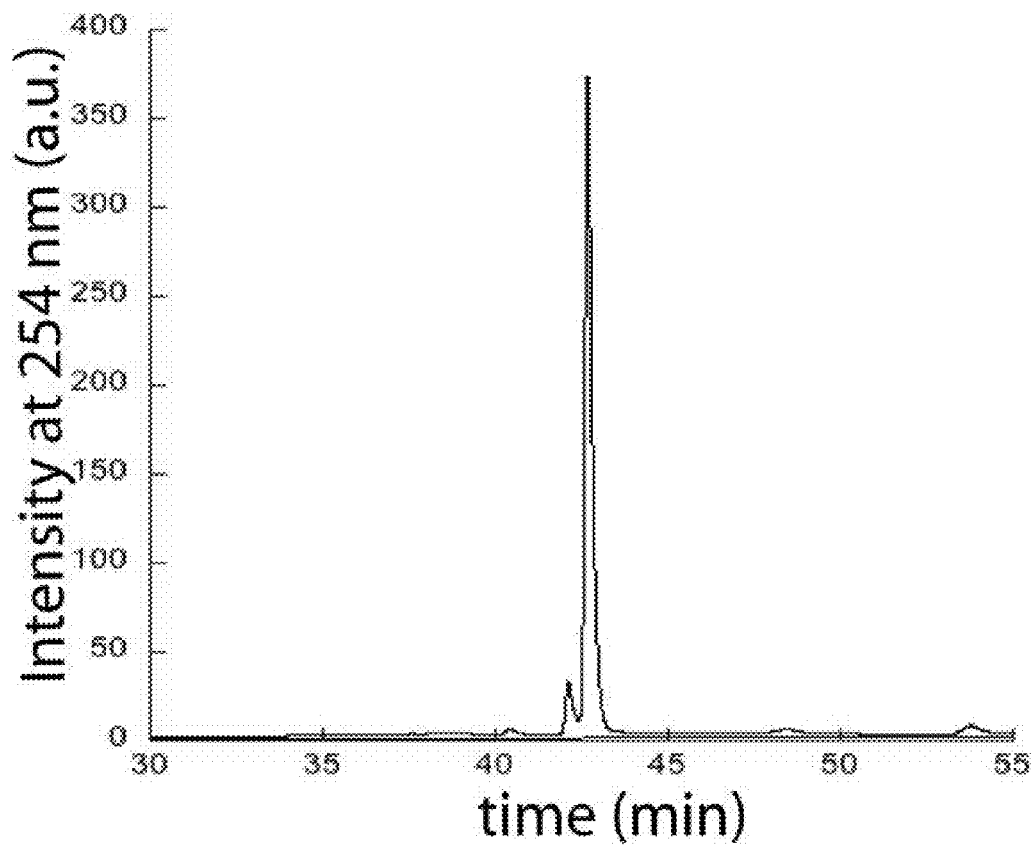
FIG. 8 shows a reverse phase high-pressure liquid chromatography spectrum using a Varian PLRP-S column at 65° C. with gradient elution (solvent A: 5% acetonitrile, 0.1M TEAA; and solvent B: 100% acetonitrile), and confirms the synthesis and isolation of the apta-chelamer of Formula 3 (AC 1). The spectrum reveals a single peak, indicating high purity.
Figure 9:
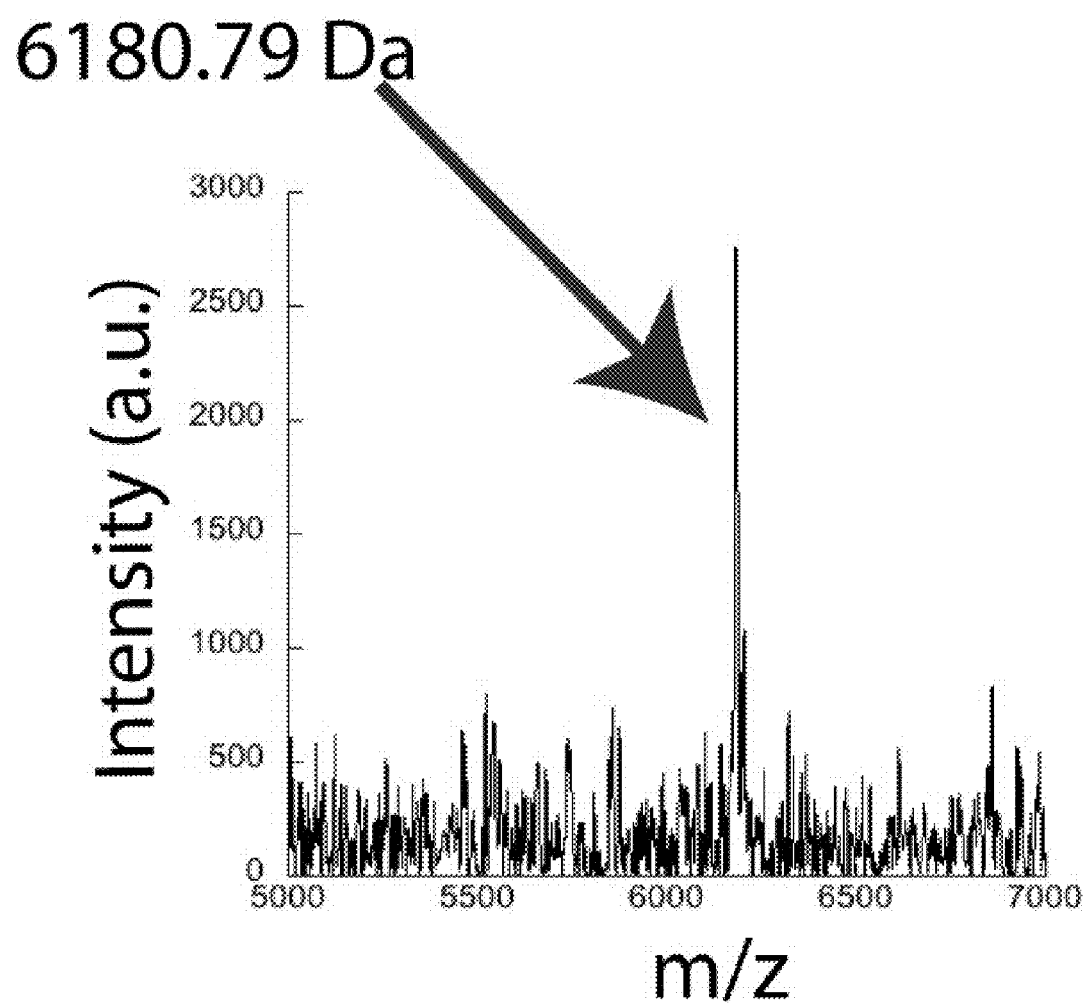
FIG. 9 shows MALDI-TOF analysis of the major peak from the FIG. 8 peak, clearly showing a dominant mass at 6180.79 Da. The calculated value for the apta-chelamer of Formula 3, AC 1, ($+Na^+$) is 6179.07 Da.
Figure 10:
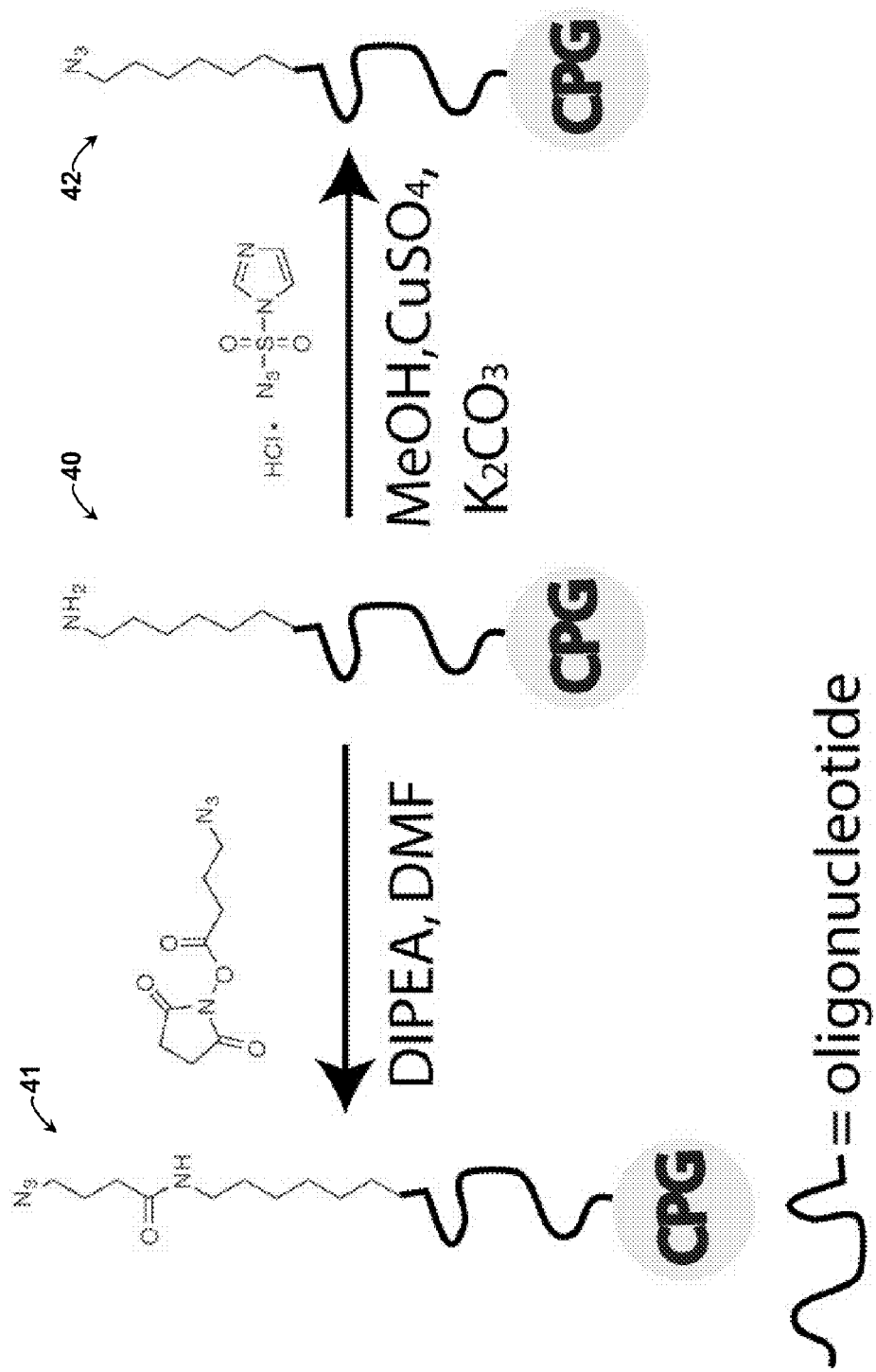
FIG. 10 shows two schematic routes for converting amine-terminated oligonucleotides (linked to CPG resin) into their azide congeners, via bifunctional linker chemistry (e.g., from compound (40) to compound (41)), or via a diazotransfer reaction (e.g., from compound (40) to compound (42)).
Figure 20A:
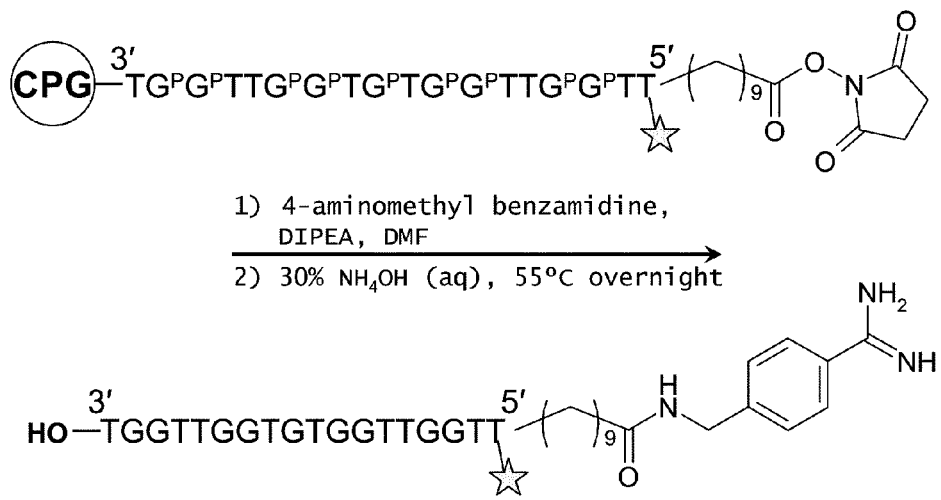
FIG. 20 shows the synthetic schemes for ODN 2 (Formula 4), via ODN 12 (FIG. 20A) and ODN 3 (Formula 5), via ODN 13 (FIG. 20B).
Figure 20B:
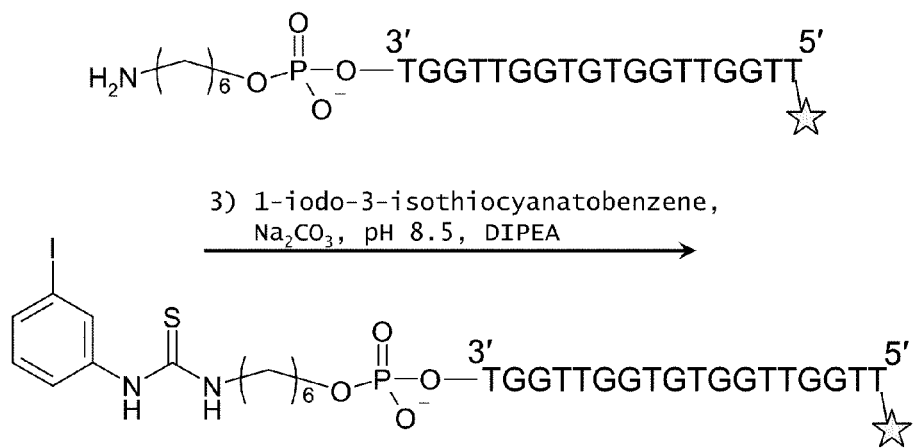

Apta-chelamer 1 was prepared by a simple two-step procedure (FIG. 7). Briefly, the core aptamer sequence (SEQ ID NO:1) bearing a C10-spacer tethered to an N-hydroxysuccinimidyl ester on the 5'-terminus and a C6-spacer linked to a phthalimide-protected amine on the 3'-terminus (which was attached to a controlled pore glass bead) (8; alternatively "ODN 8") was reacted with 4-aminomethyl benzamidine under basic conditions. The crude 5'-reacted product was cleaved from the bead, and globally deprotected using aqueous ammonium hydroxide. This deprotection step also served to cleave the phthalimide protecting group on the 3'-terminus, thus exposing a nascent primary amine (10; alternatively "ODN 10"). The 3'-terminus was then reacted with 3-iodophenylisothiocyanate to yield AC 1 (1; Formula 3). In addition to synthesizing AC 1, the present inventor also prepared a series of control ODNs (2-4) that lack one or both of the synthetic protein-binding arms. Specifically, ODN 2 (2, FIG. 20A; Formula 4) contains the same aptamer core (SEQ ID NO:1) and 5'-ba containing arm as AC 1, but lacks the 3'-ipt arm. Conversely, control ODN 3 (3, FIG. 20B; Formula 5) lacks the ba arm on the 5'-terminus but includes the ipt arm on the 3'-end and contains the same aptamer core (SEQ ID NO:1). ODN 4 (SEQ ID NO:7; Formula 6) is a double mutant with sequence 5'-TTGGTTGGTGTGGTTGGT-3' and contains no arms, so only consists of the core aptamer domain with the 5' and 3' ends each bearing an —OH group, and with the 5' terminal dT bearing a fluorescein moiety.

Core oligonucleotide (ODN) sequences 13 (FIG. 20B), 12 (FIG. 20A), 8 (FIG. 7), 7 (SEQ ID NO:5), 6 (SEQ ID NO:3), 5 (SEQ ID NO:2), and 4 (Formula 6) were synthesized by the Keck Foundation Biotechnology Resource Laboratory at Yale University using standard automated solid phase synthesis.

Note that such chemically-synthesized oligonucleotides bear —OH at both the 5' and 3' ends, instead of a 5'-OPO$_3$ and a 3'-OH. Modified phosphoramidites (5'-Carboxy-Modifier C10, 3'-PT Amino-Mod C6, Fluorescein dT, and TAMRA CPG) were purchased from Glen Research. All ODNs were purified with sephadex resin Microspin G-25 columns (GE Healthcare) and chromatographed with a Varian Prostar reverse-phase HPLC complete with MetaTherm column heater. Concentrations of stock solutions of ODNs were quantified based on their respective electronic absorption at 260 nm and their molar extinction coefficients obtained by nearest neighbor calculations. Purified ODNs were characterized by Matrix-Assisted Laser Desorption Ionization-Time of Flight (MALDI-TOF) mass spectrometry using a Bruker Daltonics Autoflex III in linear negative mode. All quadruplex forming ODNs were monitored for quadruplex formation by circular dichroism spectrophotometry (Jasco 810 Circular Dichroism System) and all data were subtracted from the spectra of a solution containing only buffer.

Precursors for the synthetic binding fragments, 4-aminomethyl benzamidine and 3-iodophenyl isothiocyanate, were purchased from Oakwood Products, West Columbia, S.C. HPLC grade acetonitrile was obtained from Alfa Aesar. Triethylammonium acetate (TEAR) was purchased from Calbiochem. Anhydrous N,N-diisopropylethylamine (DIPEA) and anhydrous DMSO were obtained from Sigma Aldrich. Trypsin from bovine pancreas was purchased from Sigma Aldrich. Unless otherwise stated all other chemicals were purchased from Sigma Aldrich.

EXAMPLE 3

Synthesis of AC 1: 5'-benzamidine Arm

As represented by FIG. 7, a solution of 5 mg of 4-aminomethyl benzamidine, 1 mL anhydrous DMSO, and 50 µL anhydrous DIPEA, was introduced by syringe to a cartridge containing ODN 8 (1.0 µmol scale) tethered to a controlled pore glass (CPG) support. Note: ODN 8 contains a 5' N-hydroxysuccinimide ester (5'-Carboxy-Modifier C10) and a 3' phthalimidyl-amino-modifier (3'-PT Amino-Mod C6). The solution containing 4-aminomethyl benzamidine was pushed through the cartridge ten times and then the CPG-linked DNA/4-aminomethyl benzamidine mixture was agitated for 1 hr. This process was repeated three times. After which, the CPG-linked DNA/4-aminomethyl benzamidine mixture was agitated overnight. After removal of the solution containing 4-aminomethyl benzamidine, the cartridge was washed with 1 mL aliquots of HPLC grade acetonitrile and dried by introducing argon flow through the cartridge for 1 hr. The 5'-modified crude oligonucleotide was cleaved and globally deprotected with 3 mL of 30% NH$_4$OH at 55° C. overnight. This deprotection step also served to cleave the phthalimide protecting group thereby introducing a nascent primary amine unit resulting in ODN 10.

EXAMPLE 4

Synthesis of AC 1: 3'-iodophenylthiourea Arm

The RP-HPLC purified ODN 10, bearing an amine at the 3'-terminus was reacted with 3-iodophenylisothiocyanate (10 mg/2 mL DMSO), DIPEA (50 µL) in 60 mM sodium carbonate buffer (pH=8.5). The solution was agitated overnight. The solvents were removed using a Savant A160 speedvac concentrator. The resulting crude residue (AC 1) was dissolved in 0.1 M TEAA buffer, desalted, purified by HPLC, and analyzed by MALDI-TOF. The synthetic scheme for aptachelamer 1 (Formula 3) is depicted in FIG. 7.

EXAMPLE 5

Synthesis of ODN Analogs 2 and 3

ODN analogs 2 and 3 (see FIGS. 20 and 21) were synthesized just as AC 1 was, as detailed in EXAMPLES 3 and 4, by reacting either the 5'-terminus of ODN 12 (FIG. 20A) to yield a 5'-benzamidine arm and ODN 2 (Formula 4) or the 3'-terminus of ODN 13 (FIG. 20B) to yield a 3'-iodophenylthiourea arm and ODN 3 (Formula 5), respectively.

EXAMPLE 6

Synthesis of ODN Analogs 4, 5, 6, and 7

ODNs 4 (Formula 6), 5 (SEQ ID NO:2), 6 (SEQ ID NO:3), and 7 (SEQ ID NO:5) were synthesized by the Keck Foundation Biotechnology Resource Laboratory at Yale University using standard automated solid phase synthesis, and were used directly (without any post-synthetic modifications) after de-salting and RP-HPLC purification.

EXAMPLE 7

Intramolecular Quadruplex and Intermolecular Duplex Formation: Standard Incubation Process for Quadruplex Formation Pure ODNs were diluted to an appropriate concentration (5 µM for CD experiments, 50 nM for FRET experiments, and 2 nM for FP experiments) in potassium containing Hepes buffer (25 mM Hepes, 20 mM KCl, 200 mM NaCl, pH 7.4) and sealed in an eppendorf tube. The tube was heated to 95° C. for 5 minutes and allowed to cool slowly to room temperature.

EXAMPLE 8

Intramolecular Quadruplex and Intermolecular Duplex Formation: Standard Incubation Process for Quadruplex-to-Duplex Transition To a solution (25 mM Hepes, 20 mM KCl, 200 mM NaCl, pH 7.4) containing preformed quadruplexes (from EXAMPLE 7, above) was added a complementary ODN sequence (such that the concentration of the complementary DNA in the mixture was equivalent to the initial quadruplex-forming strand). The resulting solution was sealed in an eppendorf tube and heated to 95° C. for 5 minutes and cooled slowly to room temperature.

EXAMPLE 9

Intramolecular Quadruplex and Intermolecular Duplex Formation: Standard Incubation Process for Duplex-to-Quadruplex Transition To a solution (25 mM Hepes, 20 mM KCl, 200 mM NaCl, pH 7.4) containing duplex DNA from EXAMPLE 8 was added one equivalent of an appropriate ODN sequence that is complementary to the sequence added in step EXAMPLE 8. The resulting solution was sealed in an eppendorf tube and heated to 95° C. for 5 minutes and cooled slowly to room temperature.

EXAMPLE 10

RP-HPLC of AC 1 and ODNs 2 Through 4

Figure 21:
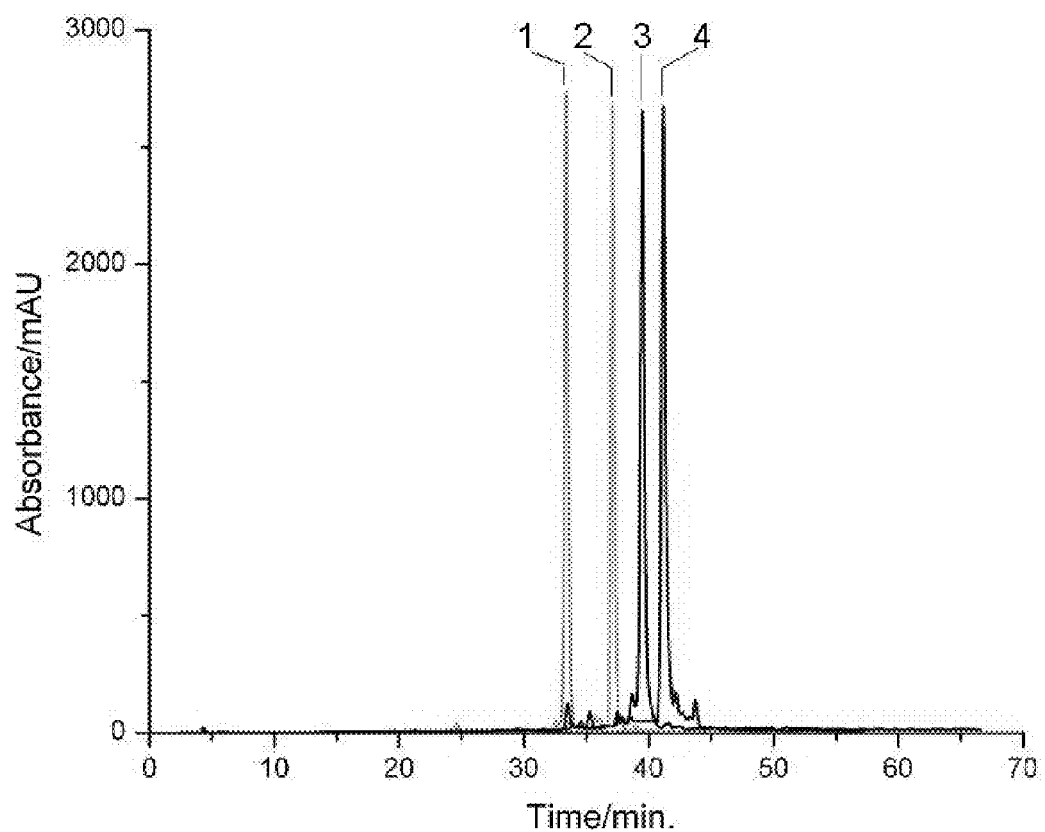
FIG. 21 shows RP-HPLC traces of AC 1 and ODNs 2 through 4 (AC 1 (Formula 3): trace number 3; ODN 2 (Formula 4): trace number 2; ODN 3 (Formula 5): trace number 4; and ODN 4 (Formula 6): trace number 1). The absorbance value was detected at 260 nm.

RP-HPLC purification was achieved using a Varian Prostar HPLC system, equipped with a Polymer Laboratories 100 Å 5 µm PLRP-S reverse phase column. The column was maintained at 65° C. for all runs. The elution gradient is given below in TABLE 1, where solvent A is 0.1 M TEAA in 5% acetonitrile and solvent B is 100% acetonitrile. RP-HPLC traces of purified ODNs (1-4) are shown in FIG. 21.

TABLE 1

| HPLC eluent gradient used for the purification of modified ODNs | | | |
|---|---|---|---|
| Time (min) | Flow (mL/min) | % A | % B |
| 0.00 | 0.750 | 100 | 0 |
| 5.00 | 0.750 | 100 | 0 |
| 25.00 | 0.750 | 90 | 10 |
| 35.00 | 0.750 | 80 | 20 |
| 45.00 | 0.750 | 60 | 40 |
| 65.00 | 0.750 | 50 | 50 |
| 70.00 | 0.750 | 0 | 100 |

EXAMPLE 11

MALDI-TOF Characterization of AC 1 and ODNs 2 Through 4

MALDI-TOF spectra were collected using a 9:1:1 matrix of 2,4,6-trihydroxyacetophenone (THAP) (10 mg/mL in 1:1 acetonitrile/water), ammonium citrate (50 mg/mL in water, 1% TFA), and oligonucleotide. The Bruker Daltonics Autoflex III was in linear negative mode, using a pulsed ion extraction time of 200 ns, and a detector voltage of 20 kV. The single stranded ODN 5'-GTGGGTAGGGCGGGTTGG-3' (SEQ ID NO:8; mass: 5707.8 Da) was used as an internal standard. Observed and predicted mass to charge (m/z) values are given below in TABLE 2.

TABLE 2

| MALDI data for synthetically modified ODNs after RP-HPLC purification | | | |
|---|---|---|---|
| ODN | Structure | Observed m/z | Predicted m/z |
| AC1 | Formula 3 | 6990.7 | 6992.3 |
| ODN2 | Formula 4 | 6632.1 | 6635.5 |
| ODN3 | Formula 5 | 6624.7 | 6630.5 |
| ODN4 | Formula 6 | 6178.1 | 6174.3 (Na$^+$ adduct) |

Figure 12:
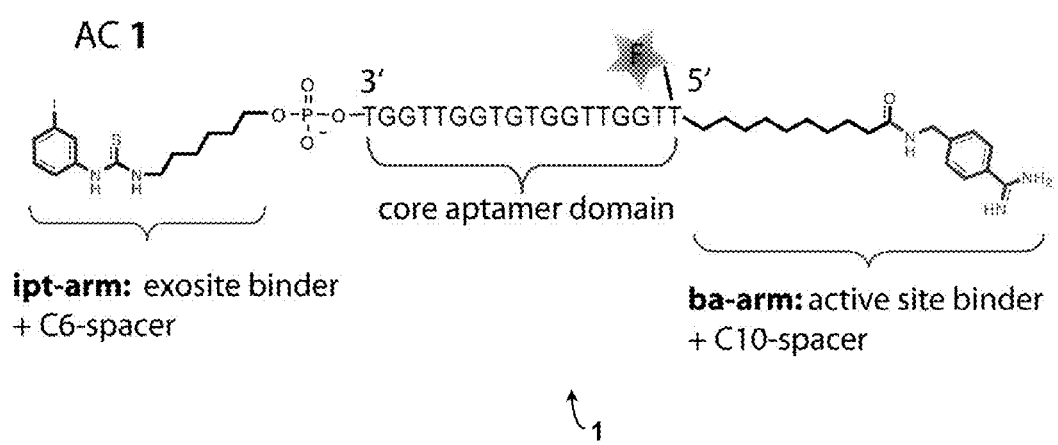
FIG. 12 shows the design of AC 1, which is identical to Formula 3 and compound (I). The core aptamer domain consists of oligonucleotide sequence SEQ ID NO:1 (5'-TTGGT-TGGTGTGGTTGGT-3'). The terminal dT on the 5' end is attached to fluorescein (star). The 5' end is further tethered to a benzamidine derivative (an active site binder) via a C10 spacer ("ba arm"). The 3' terminus is attached to an iodophenylthiourea exosite binder via a C6 linker ("ipt arm"). As explained above for FIG. 11, the star containing "F" represents an optional fluorescein moiety. The fluorescein moiety need not be present, or may be replaced with a different fluorophore, chromophore, or other detectable label.

Formula 3 of TABLE 2 is:
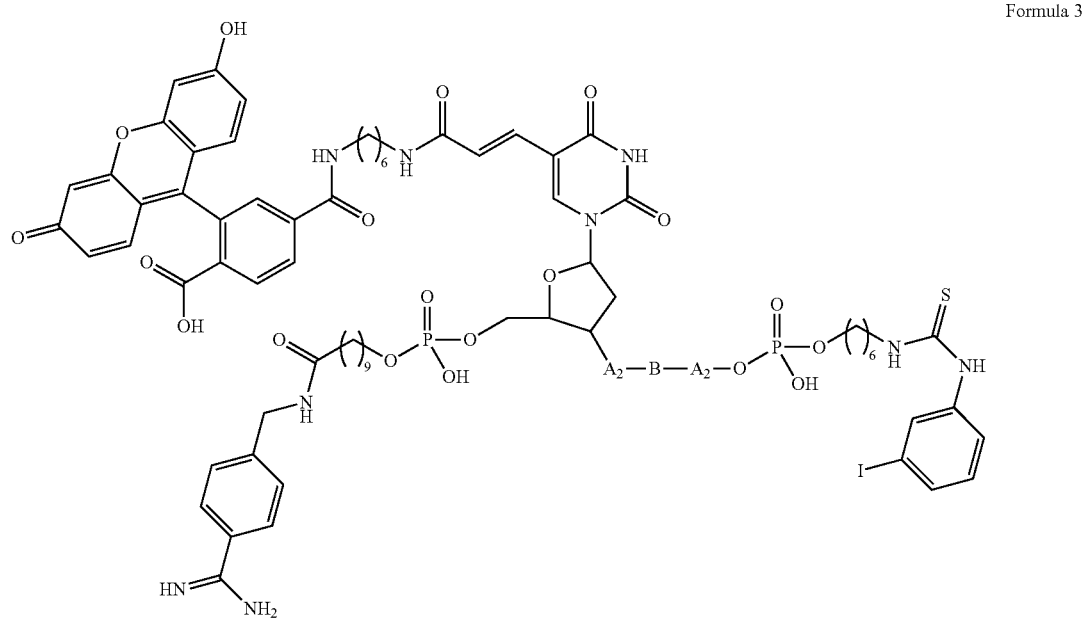
Formula 3
wherein "A" of Formula 3 is Formula 7:
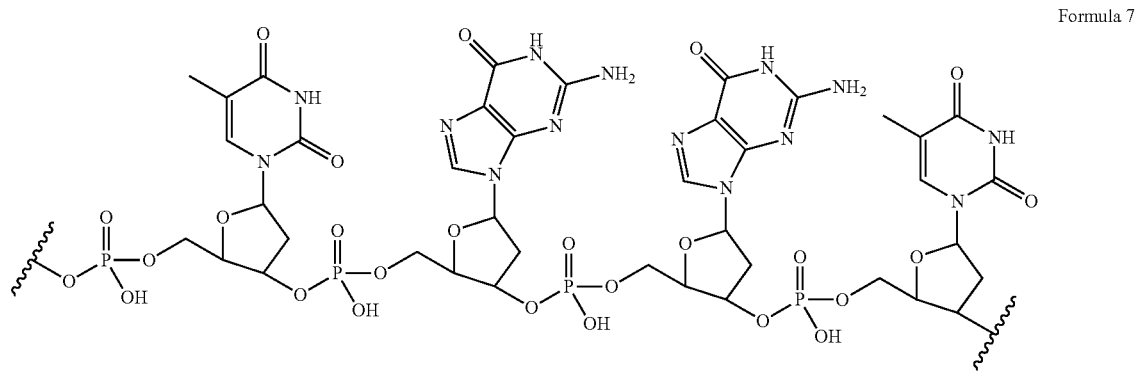 [SMILES: *OP(=O)(O)OCC1OC(n2cc(C)c(=O)[nH]c2=O)CC1OP(=O)(O)OCC1OC(n2cnc3c(=O)[nH]c(N)nc32)CC1OP(=O)(O)OCC1OC(n2cnc3c(=O)[nH]c(N)nc32)CC1OP(=O)(O)OCC1OC(n2cc(C)c(=O)[nH]c2=O)CC1*]
Formula 7
and wherein "B" of Formula 3 is Formula 8:

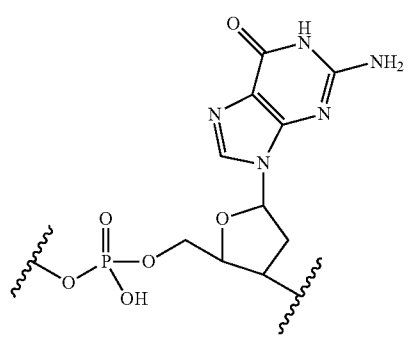
Formula 8
As will be appreciated by those of ordinary skill in the art, and as shown in FIG. 12, Formula 3 can be written in abbreviated form using standard one-letter abbreviations for the deoxynucleotide bases.
Formula 4 of TABLE 2 is:
Formula 4
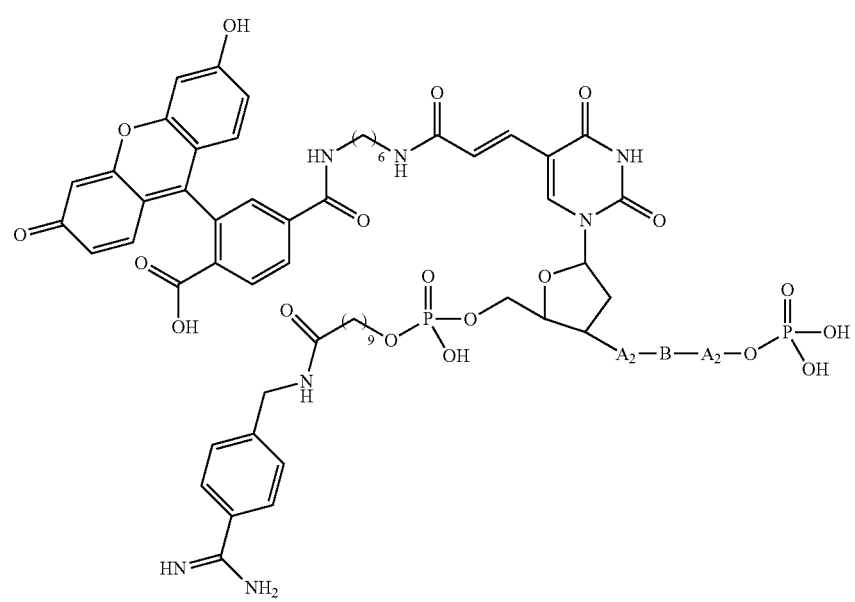
Formula 5 of TABLE 2 is:
Formula 5
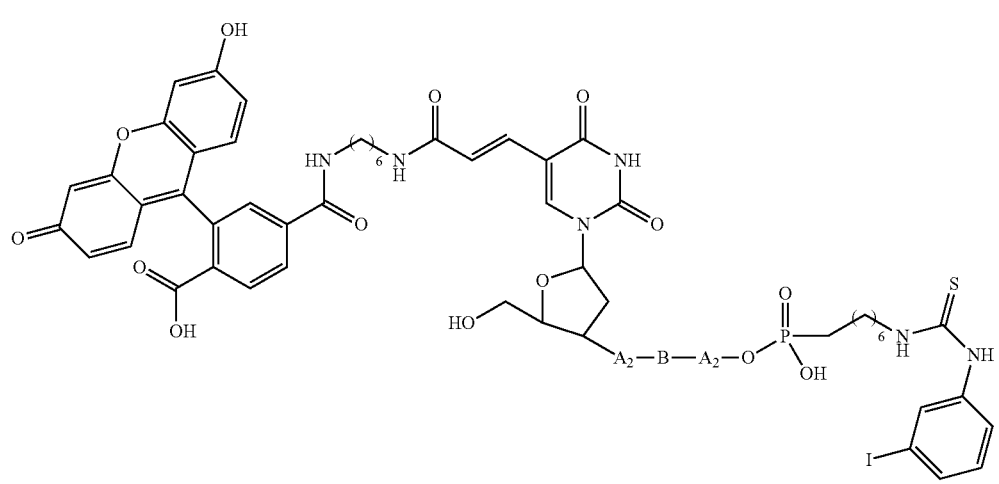

wherein "A" is Formula 7, and wherein "B" is Formula 8.
Formula 6 of TABLE 2 is:

Formula 6

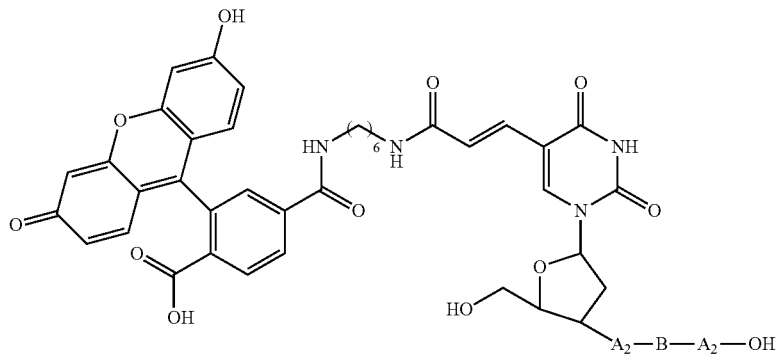

wherein "A" is Formula 7, and "B" is Formula 8.

As seen in Formulae 3 through 6 (AC 1 and ODNs 2-4, respectively), the oligonucleotide sequences each bear an optional fluorescein moiety (shown by Formula 9) attached to the 5'-terminal deoxythymidine.

Formula 9

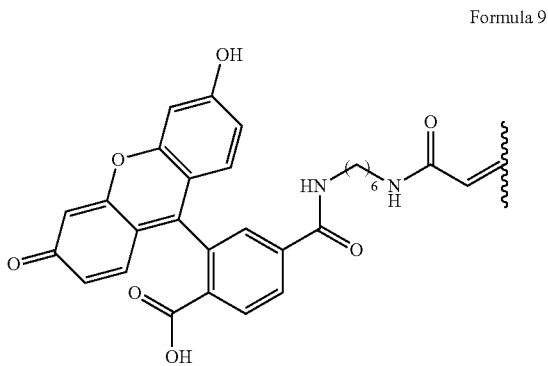

As will be appreciated by those of ordinary skill in the art, the fluorescein moiety in any of the embodiments of the present invention may be omitted or may be replaced with a different fluorescent or colorimetric moiety. For example, if the fluorescein moiety were omitted from Formula 6, the structure of Formula 6 would become that of Formula 10:

Formula 10

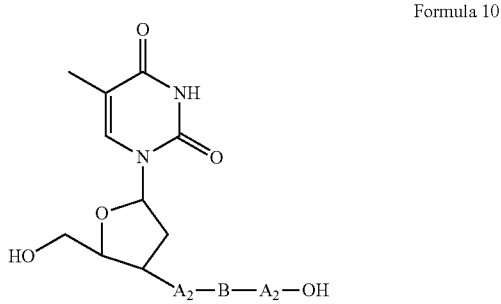

EXAMPLE 12

SDS-PAGE

Figure 19:
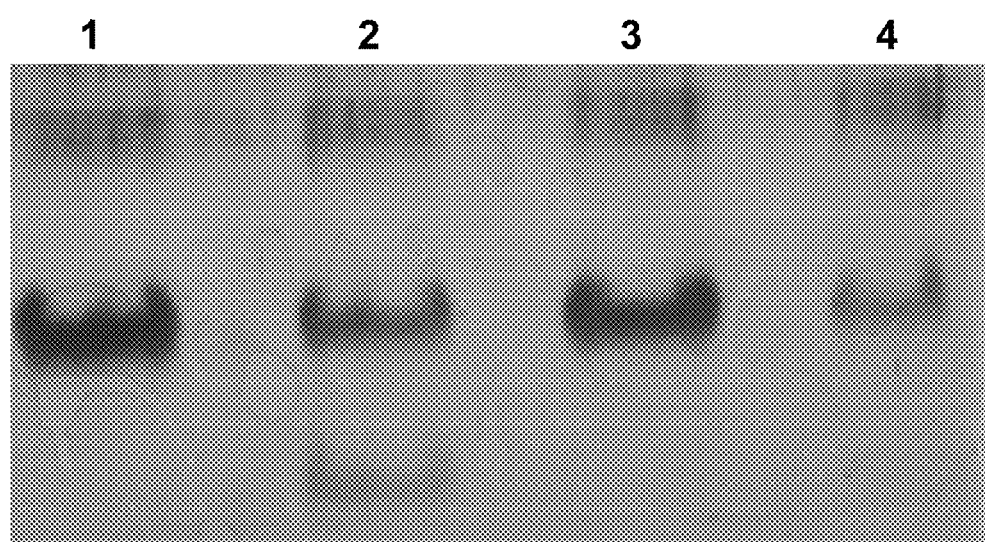
FIG. 19 shows bands from lanes 1 through 4 of the native gel shown in FIG. 18, which were excised and resolved subsequently via SDS-PAGE (sodium dodecyl sulfate polyacrylamide gel electrophoresis—SDS is an anionic detergent which denatures secondary and non-disulfide linked tertiary structures). As seen from the lower band of lane 2, only modified m-TBA formed a three-component complex (i.e., m-TBA:thrombin:trypsin).

SDS-PAGE was performed according to the method of Laemmli (1970). A 15 μl aliquot of the eluate was mixed at 1:1 (v/v) ratio with the SDS-PAGE sample buffer (Bio-Rad) and heated at 100° C. for 4 minutes. The samples were applied onto a gel made of 4% stacking and 12% resolving gels, and subjected to electrophoresis at a constant voltage of 200V for 50 minutes. The running buffer was 1×Tris/Glycine/SDS (Bio-Rad), containing 0.025 M Tris, 0.19 M glycine and 0.1% SDS at pH 8.3. After electrophoresis, the gels were visualized using a silver stain (from Pierce), as shown in FIG. 19.

EXAMPLE 13

Characterization of ACs Via Circular Dichroism

Figure 22:
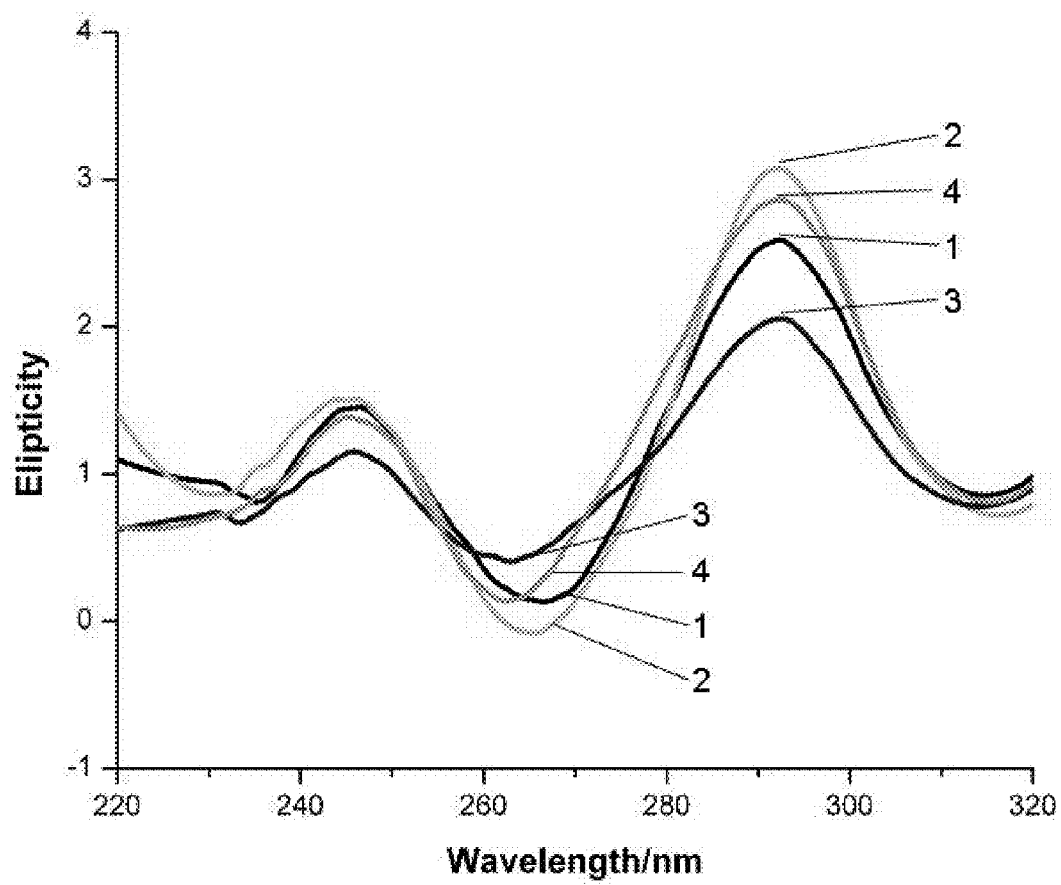
FIG. 22 shows circular dichroism spectra of AC 1 and ODNs 2 through 4 upon exposure to quadruplex forming conditions. Individual spectra for AC 1 and ODNs 2 through 4 are labeled accordingly.

Prior to performing any trypsin-binding studies, circular dichroism (CD) experiments were undertaken to probe the ability of AC 1 (and control ODNs 2 through 4) to form an intramolecular quadruplex that would enable bidentate binding to trypsin (see FIG. 22). Formation of an intramolecular quadruplex was achieved using a standard quadruplex-folding procedure (i.e. heating and cooling in the presence in the presence of templating potassium cations, 20 mM KCl, 200 mM NaCl, 25 mM Hepes, pH 7.4). The quadruplex-forming buffer also contained 200 mM NaCl because this high-salt concentration was necessary for subsequent trypsin-binding experiments. In particular, high NaCl concentration is required to attenuate non-specific binding between trypsin and the aptamer core (as explained further below). This protocol resulted in a characteristic CD profile for an anti-parallel intramolecular quadruplex with a positive ellipticity at 292 nm and a negative ellipticity at 266 nm. See P. A. Rachwal, I. S. Findlow, J. M. Werner, T. Brown, K. R. Fox. *Nucleic Acids Res.* 2007, 35, 4214-4222, incorporated by reference herein in its entirety. Similar CD profiles were observed for control ODNs 2 through 4.

CD spectra were collected at 25° C. using a Jasco J-810 spectropolarimeter in a 2 mm path length cell with a response time of 1 second, a data pitch of 0.1 nm, and a scan speed of 100 nm/min. All measurements were carried out in 20 mM KCl, 200 mM NaCl, 25 mM Hepes, pH 7.4. Concentrations of all ODNs were 5 μM. The results of FIG. 22 clearly show the presence of a positive ellipticity at 292 nm and a negative ellipticity at 266 nm for AC 1 and ODNs 2 through 4 (with each curve labeled accordingly) upon exposure to quadruplex forming conditions. These values are characteristic of antiparallel quadruplexes formed by an intramolecular quadruplex.

EXAMPLE 14

Characterization of ACs Via Fluorescence Anisotropy

Figure 14:
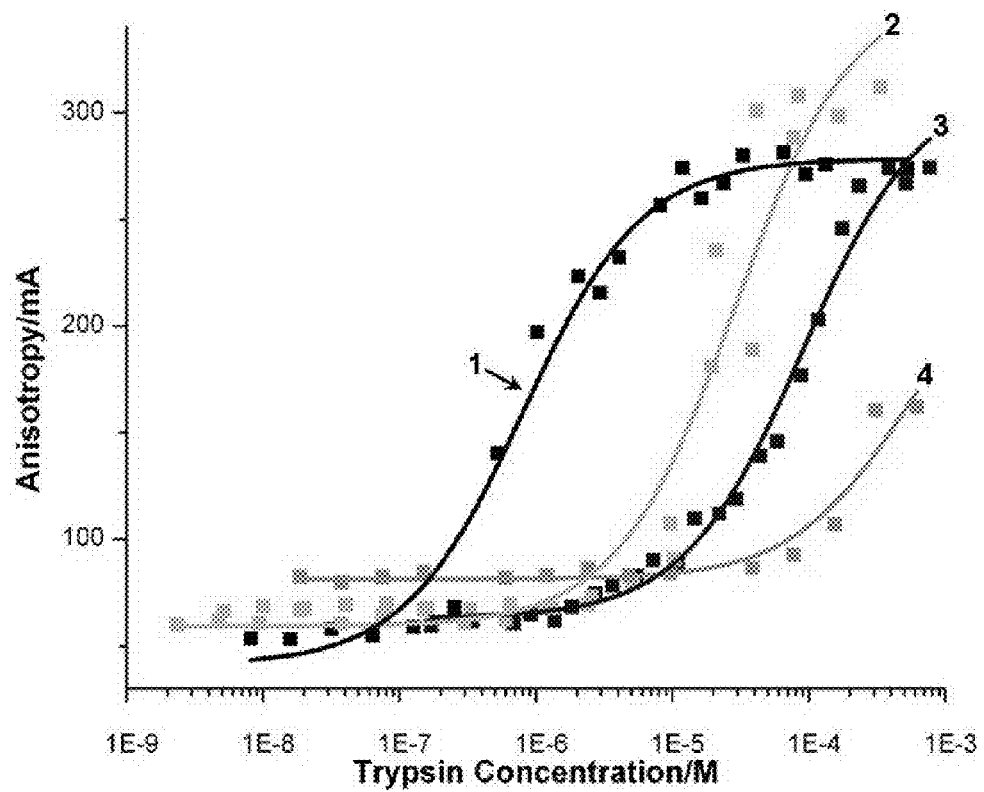
FIG. 14 shows the results of fluorescence anisotropy studies of AC 1 and ODNs 2, 3, and 4 in the presence of increasing trypsin concentration in 25 mM KCl, 200 mM NaCl, 25 mM Hepes, pH 7.4. Curves 1, 2, 3, and 4 correspond to AC 1 and ODNs 2, 3, and 4, respectively. AC 1 is sometimes referred to herein as ODN 1. All trypsin binding studies were performed on the preformed intramolecular quadruplex conformation of the ODNs (25 mM KCl, 200 mM NaCl, 25 mM Hepes, pH 7.4). The concentration of each ODN was 2 nM.

The next step was to determine whether the intramolecular quadruplex conformation of AC 1 leads to enhanced affinity towards trypsin as a result of bidentate binding (FIG. 15, pathway A). Hence, fluorescence anisotropy titrations were undertaken. AC 1 and ODNs 2 through 4 were first incubated in the presence of potassium cations to induce the quadruplex fold. The preformed quadruplexes were then incubated with increasing concentrations of trypsin at 25° C. (25 mM KCl, 200 mM NaCl, 25 mM Hepes, pH 7.4) for 30 min. Preliminary fluorescence anisotropy studies were conducted to ascertain that equilibrium was reached after 30 min and that there was no significant quenching of the fluorescein emission. The anisotropy associated with the fluorescein emission was followed at 525 nm (excitation at 495 nm). The resultant binding isotherms (FIG. 14) were fitted using non-linear regression to a 1:1 binding stoichiometry. The dissociation constant ($K_d$) for control ODN 2 (containing the ba-arm on the 5'-terminus) was found to be $2.9 \times 10^{-5}$ M. Monodentate control ODN 3 (possessing only the ipt-arm on the 3'-terminus) displayed weaker binding to trypsin ($K_d=9.0 \times 10^{-5}$ M). In striking contrast, the $K_d$ for bidentate AC 1 was found to be substantially stronger than either control systems. In fact, the dissociation constant was determined to be $8.1 \times 10^{-7}$ M, a value that indicates a greater than 100 and 30 fold binding enhancement when compared to monodentate controls ODN 3 and ODN 2, respectively. These results clearly indicate that bidentate binding, as a result of intramolecular quadruplex formation, dramatically enhances the affinity of AC 1 to trypsin. Importantly, the ODN 4 negative control, which lacks both binding arms, displayed only a weak trypsin-binding ability ($K_d=2.9 \times 10^{-3}$ M). This dissociation constant is attributed to non-specific interactions between bovine trypsin and ODN 4, since trypsin (pI=10.5) is positively charged at pH=7.4 and thus can potentially associate with the negatively charged DNA backbone. Support for such non-specific interactions comes from incubation of trypsin with ODN 4 where the concentration of salts were decreased to only 5 mM KCl, 25 mM Hepes, pH 7.4 (see, e.g., FIG. 23). This resulted in a significant decrease in the $K_d$, while a similar experiment with AC 1 displayed only slight change in affinity.

EXAMPLE 14

Competition Assay—Fluorescence Resonance Energy Transfer (FRET) Studies (AC 1 and ODN 7)

In addition to forming a well-folded quadruplex structure in the presence of potassium, the thrombin-binding aptamer has also been demonstrated to form a thermodynamically more favorable double helix in the presence of a complementary DNA sequence (N. Kumar, S. Maiti. *Biochem. Bioph. Res. Corn.* 2004, 319, 759-767, incorporated by reference herein in its entirety.). Thus, the present inventor reasoned that incubation of AC 1 (in its intramolecular quadruplex conformation) with an appropriate complementary strand could result in the formation of a duplex structure that necessarily projects the ba and ipt-arms in opposite directions (FIG. 15, pathway B). This conformational switch could significantly decrease the trypsin-binding ability of AC 1.

Immediately prior to each fluorescence polarization experiment, fresh stock solutions of trypsin were made in Hepes buffer (20 mM KCl, 200 mM NaCl, 25 mM Hepes, pH 7.4). Concentration of the trypsin in the stock solutions were determined using ultra-violet absorbance at 280 nm ($\epsilon=37669$ $M^{-1}cm^{-1}$). Serial dilutions from the stock solution of trypsin were made into eppendorf tubes (spanning a range from $1 \times 10^{-9}$ to $1 \times 10^{-3}$ M). To these trypsin-containing tubes were added aliquots of ODNs, such that the total concentration of ODNs in each eppendorf tube was 2 nM. After gently agitating, 150 uL from each eppendorf was transferred to respective borosilicate glass culture tubes and the tubes were allowed to equilibrate for 30 minutes at 25° C. (preliminary fluorescence anisotropy studies were conducted to ascertain that equilibrium was reached after 30 min and that there was no significant quenching of the fluorescein emission). Fluorescence polarization at 25° C. was determined on a Molecular Probes Beacon 2000 Fluorescence Polarization Instrument, using 495 and 525 nm narrow band pass filters for excitation and emission, respectively. Values of millipolarization (mP) from the Beacon 2000 were converted to millianisotropy (mA) using equation 1, where A is the anisotropy value, and P is the observed polarization.

$$A = \frac{2P}{3-P} \quad \text{Equation 1}$$

1:1 (trypsin:ODN) binding mode: Anisotropy was plotted against trypsin (receptor protein) concentration and fitted to Equation 2 (a single-site model without receptor depletion), wherein $A_f$ is the anisotropy of the unbound ODN, $A_b$ is the anisotropy of the bound ODN, $O_r$ is the total added ODN concentration (in M units), and $K_d$ is the dissociation constant. Non-linear regression analysis using Origin 8.0 software was used for fitting the experimental data.

$$A = A_f + \left[ (A_b - A_f) \times \frac{O_\tau}{K_d + O_\tau} \right] \quad \text{Equation 2}$$

Cooperative binding mode: Binding equilibrium best described as cooperative binding was fitted to the Hill equation (Equation 3), where the fluorescence quantum yield of fluorescein is constant and the ODN substrate is limiting. R is the total protein concentration, $R_{1/2}$ (or $[\text{trypsin}]_{1/2}$) is the protein concentration required for half-maximal binding, and h is the Hill coefficient.

$$A = A_f + (A_b - A_f) \times \left( \frac{\left(\frac{R}{R_{\frac{1}{2}}}\right)^h}{1 + \left(\frac{R}{R_{\frac{1}{2}}}\right)^h} \right) \quad \text{Equation 3}$$

Figure 16:
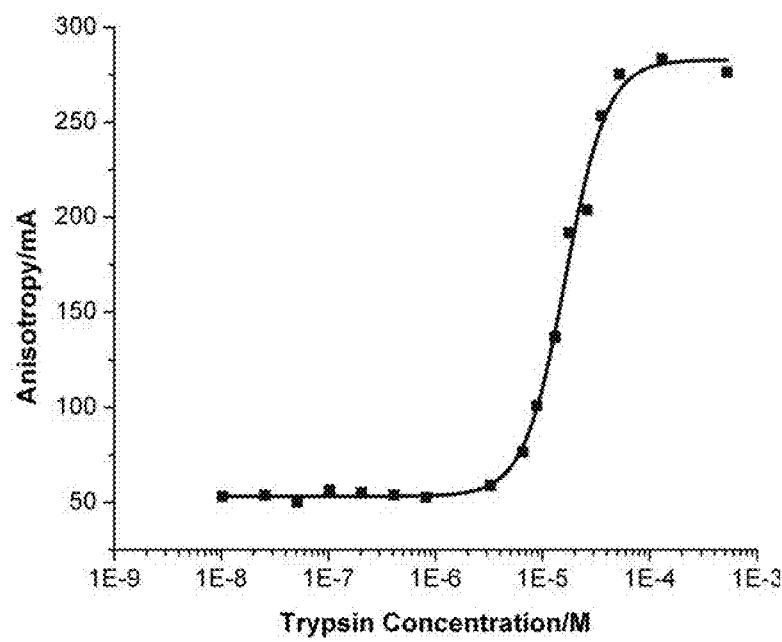
FIG. 16 shows the results of fluorescence anisotropy titration of AC 1 (2 nM) first incubated with ODN 5, to give duplex 1:5, followed by addition of increasing trypsin concentrations.

The results of FIG. 16 show fluorescence anisotropy titration of AC 1 (2 nM) first incubated with complementary strand 5, to give duplex (1:5), followed by addition of increasing trypsin concentrations. All studies were conducted at 20 mM KCl, 200 mM NaCl, 25 mM Hepes, pH 7.4. The raw data is depicted by squares (■) and the line connecting the squares is the non-linear curve fit. The raw data was fitted ($R^2$=0.99) with equation 3, giving a Hill coefficient of 2.2 and a [trypsin]$_{1/2}$ of $1.6\pm0.1\times10^{-5}$M.

Figure 23:
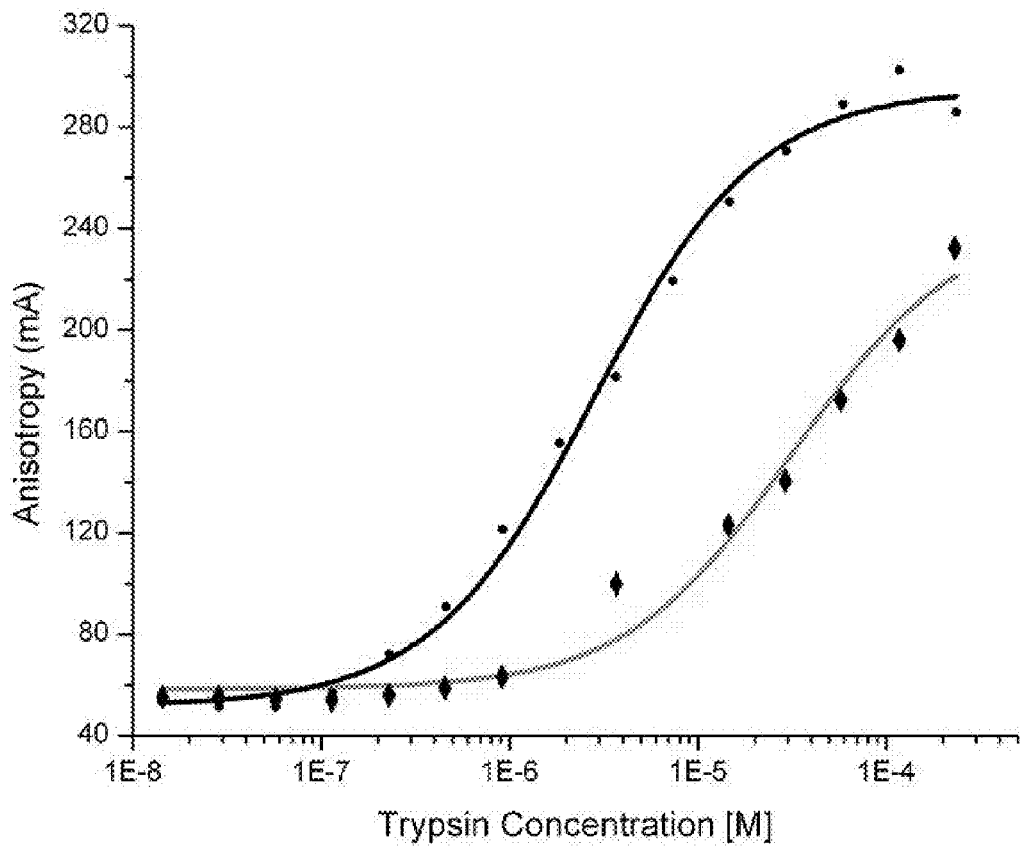
FIG. 23 shows the results of fluorescence anisotropy titrations of AC 1 and negative control ODN 4 (2 nM) (Formula 6), first exposed to quadruplex-forming conditions and followed by incubation with increasing concentrations of trypsin. These experiments were conducted under low-salt conditions (5 mM KCl, 25 mM Hepes, pH 7.4).

The results of FIG. 23 show fluorescence anisotropy titrations of AC 1 and negative control ODN 4 (2 nM), first exposed to quadruplex forming conditions followed by incubation with increasing concentrations of trypsin. These experiments were conducted under low-salt conditions (5 mM KCl, 25 mM Hepes, pH 7.4. The raw data is depicted by circles (●) for AC 1 and diamonds (♦) for ODN 4. The lines represent non-linear fits to equation 2 ($R^2$=0.99 for AC 1 and 0.98 for ODN 4).

Non-linear regression analysis using Equation 2 resulted in a dissociation constant of $3.1\pm0.7\times10^{-5}$M for ODN 4 with trypsin, under low salt conditions (5 mM KCl, 25 mM Hepes, pH 7.4). This value is significantly lower than the analogous $K_d$ ($2.9\pm1.8\times10^{-3}$M) under high-salt conditions (20 mM KCl, 200 mM NaCl, 25 mM Hepes, pH 7.4). These findings are consistent with the fact that bovine trypsin is positively charged at pH=7.4 (pI of bovine trypsin is=10.5) and thus can potentially associate with the negatively charged ODN backbone, through non-specific interactions, under low-salt conditions. Furthermore, analogous experiments with specific bidentate binder AC 1 displayed only a slight change in the dissociation constant under low-salt conditions ($K_d$=$2.8\pm0.3\times10^{-6}$ M).

While CD experiments clearly indicated the formation of a quadruplex for AC 1 and ODNs 2 through 4, the concentrations required for CD studies (5 μM) are much greater than those used for FP studies (2 nM). Thus, we verified the transition from quadruplex-to-duplex using FRET studies. These experiments were conducted on a Varian Cary Eclipse Fluorescence Spectrophotometer. The excitation wavelength was set to 480 nm (5 nm slit) to minimize TAMRA co-excitation. Emission was monitored from 500 to 600 nm (5 nm slit). Here. ODN 7 (SEQ ID NO:5; 5'-ACCAACCACAC-CAACCA-3') was used as the complementary strand. The TAMRA moiety is conjugated (via a precursor linked to a CPG bead) directly to the 3' phosphate of adenosine ODN 7 is identical to ODN 5 but also contains a tetramethylrhodamine (TAMRA) fluor (X) on the 3'-terminus.

Figure 24:
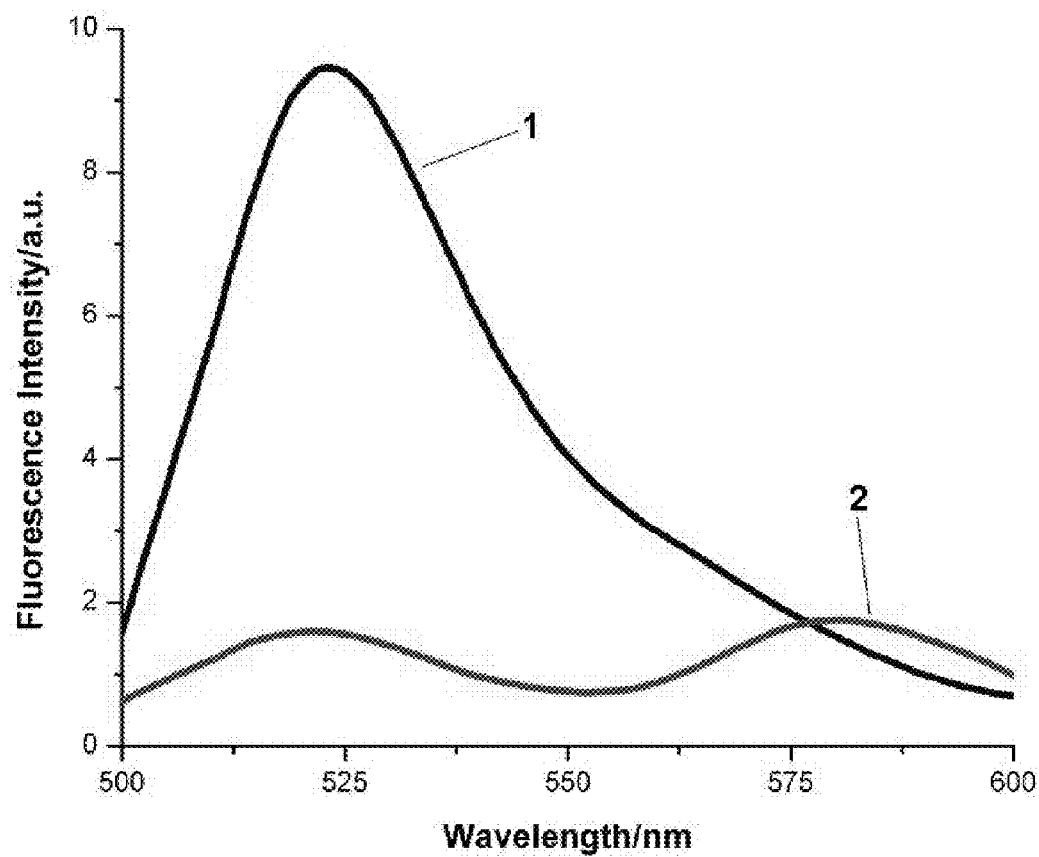
FIG. 24 shows the results of FRET studies of a solution containing preformed quadruplex AC 1, (line 1), and AC 1 upon incubation with 1.25 equivalents of ODN 7 (line 2) (SEQ ID NO:5).

FIG. 24 shows the results of FRET studies of a solution containing preformed quadruplex AC 1, (line 1), and AC 1 upon incubation with 1.25 equiv. of ODN 7 (line 2). All studies were conducted at 20 mM KCl, 200 mM NaCl, 25 mM Hepes, pH 7.4. The concentration of AC 1 was 50 nM.

Incubation of AC 1 with ODN 7 resulted in significant quenching of the fluorescein emission (centered at 525 nm) of 1. Further, an isoemissive point at 578 nm and a concomitant increase in the TAMRA emission of 7 at 580 nm (albeit small) are also observed. These findings can be best explained by duplex formation (1:7) leading to FRET from the fluorescein moiety of 1 to the TAMRA moiety of 7. Furthermore, these FRET profiles are in clear agreement with previous literature reports using these same fluor pairs and the 15-mer thrombin-binding aptamer.

In order to test whether a double helix composed of 1 leads to diminished trypsin-binding, a 17-mer complementary strand ODN 5 (SEQ ID NO:2; 5'-ACCAACCACAC-CAACCA-3') was chosen. ODN 5 is capable of forming Watson-Crick base-pairs with all except the terminal 5' (fluorescein containing dT) residue on AC 1. AC 1, in the quadruplex conformation, was first annealed with one equivalent of ODN 5 (FIG. 15, pathway B) followed by incubation with increasing concentrations of trypsin (FIG. 15, pathway D). Evidence for duplex formation came from FRET studies using a fluorescent congener of ODN 5, as described above.

The titration of duplex 1:5 with trypsin was followed by fluorescence anisotropy and the resulting binding profile (FIG. 16) was fitted to the Hill equation (E. J. Fialcowitz-White, B. Y. Brewer, J. D. Ballin, C. D. Willis, E. A. Toth, *J. Biol. Chem.* 2007, 282, 20948-20959.). From this fit, a Hill coefficient (h) of 2.2 was obtained, a finding that supports the notion that duplex 1:5 binds to two molecules of trypsin (i.e., one binding site on each end of the duplex) with positive cooperativity. Furthermore, the concentration of trypsin that yields half-maximal binding ([trypsin]$_{1/2}$) was determined to be $1.6\pm0.1\times10^{-5}$M. Comparison of this value with the $K_d$ of preformed quadruplex 1 (i.e., $8.1\times10^{-7}$ M) indicates that the quadruplex form is about 20 times more potent in binding to trypsin than the double helical structure.

Figure 17:
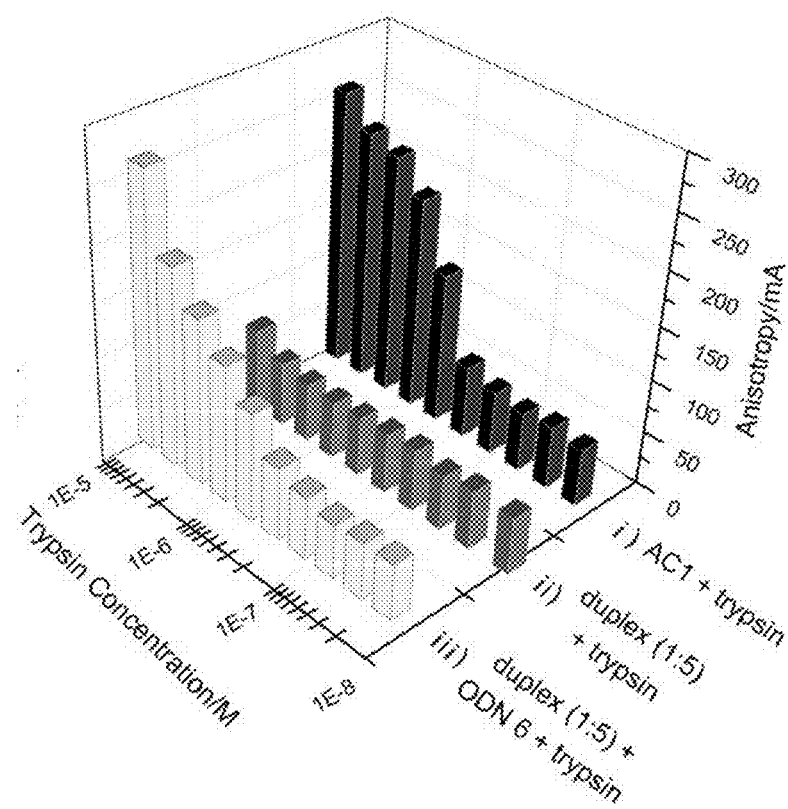
FIG. 17 is a bar-graph illustrating the increase in fluorescence anisotropy as trypsin binds to (i) AC 1, (ii) duplex (1:5), and (iii) duplex (1:5) incubated with ODN 6. All binding studies were performed in 20 mM KCl, 200 mM NaCl, 25 mM Hepes, pH 7.4. The concentration for each of ODNs 1, 5, and 6 was 2 nM.

A further versatility of such structure-switching aptamers is their ability to be cycled. Thus duplex 1:5 can potentially be reverted back to the quadruplex form by incubation in the presence of potassium ions and another ODN that can form a stronger duplex with ODN 5 (FIG. 15, pathway C) (P. Alberti, J.-L. Mergny, *Proc. Natl. Acad. Sci. U.S.A.* 2003, 100, 1569-1573, incorporated by reference herein in its entirety). Thus, the present inventor incubated duplex 1:5 with one equivalent of ODN 6 (SEQ ID NO:3; 5'-TGGTTGGTGTGGTTGGT-3') which is identical in DNA sequence to ODN 1 but does not possess the 5'-fluorescein containing dT residue (ODN 6 also does not include either of the binding arms found in AC 1). Hence, ODN 6 should form a perfect duplex with ODN 5. To the resulting solution was added increasing concentrations of trypsin (See FIG. 17, iii). Interestingly, this latter fluorescence anisotropy profile matched closely with the one obtained for preformed quadruplex AC 1 in the presence of trypsin (FIG. 17, i). Taken together, these results clearly indicate that incubation of duplex 1:5 with ODN 6 reverts a significant amount of AC 1 back to the quadruplex form, which in turn, sequesters trypsin in a bidentate fashion.

EXAMPLE 15

Apta-Chelamer Characterization Via PAGE 0.0817 nmol of m-TBA (which is identical to AC 1 minus the dT-fluorescein residue on the 5'-end) or TBA (SEQ ID NO:4; 5'-TGGTTGGTGTGGTTGGT-3', i.e., same sequence as mTBA but contains no arms or spacers) was incubated with 0.0817 nmol of thrombin in PBS (pH 7.5) at room temperature (R.T.) for 30 minutes, followed by addition of 0.0817 nmol of trypsin and 4.1 of NaCl PBS solution (final concentration of NaCl was 500 mM). The samples were preincubated at R.T. for another 30 minutes, then resolved via polyacrylamide gel electrophoresis using a 6% native polyacrylamide gel and 1×Tris/Glycine buffer, for 4 h at a constant voltage of 40V at R.T. The gel was then stained with Coomassie Blue to visualize protein bands, and destained via standard laboratory procedures to reduce background staining. The results are shown in FIG. 18.

Figure 18:
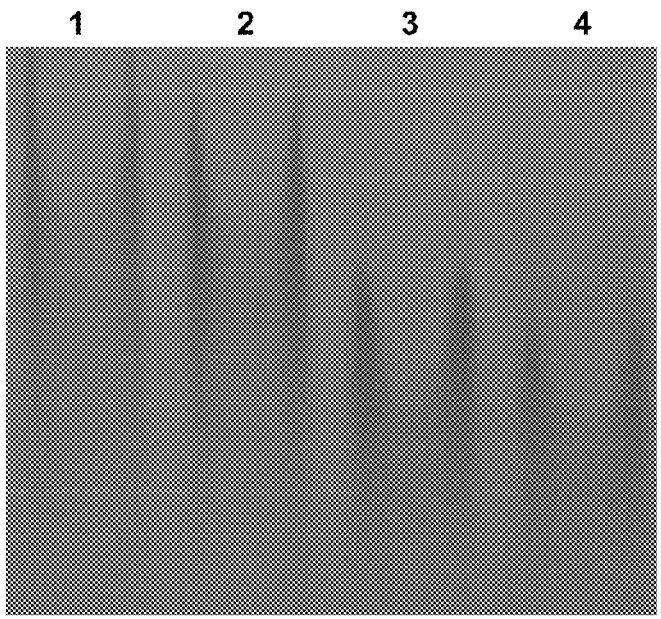
FIG. 18 shows the resolution of m-TBA and TBA via native polyacrylamide gel electrophoresis (PAGE). Gel conditions: 6% native polyacrylamide gel and 1×Tris/Glycine running buffer. The gel was then stained with Coomassie Blue to visualize protein bands. Lanes 1 and 2 contain m-TBA, which is identical to AC 1 minus the dT-fluorescein residue on the 5'-end. Lanes 3 and 4 contain TBA (SEQ ID NO:4; 5'-TG-GTTGGTGTGGTTGGT-3', which is the same sequence as m-TBA but contains no arms and no spacers). Lane 1 contains m-TBA and thrombin in a 1:1 ratio. Lane 2 contains m-TBA, thrombin, and trypsin in a 1:1:1 ratio. Lane 3 contains TBA and thrombin in a 1:1 ratio. Lane 4 contains TBA, thrombin, and trypsin in a 1:1:1 ratio.

Gel bands from the gel of FIG. 18 were excised, cut into small pieces, placed in microcentrifuge tubes, and incubated in elution buffer (50 mM Tris-HCl, 150 mM NaCl, 0.1% SDS, 2 mM EDTA, pH 7.5) on a shaker overnight. The eluate was condensed using a speed-vac and 15 aliquots were tested by SDS-PAGE (FIG. 19). The protein bands of lanes 1, 2, 3, and 4 in FIG. 19 correspond to the protein bands of lanes 1, 2, 3, and 4, respectively, of FIG. 18. As FIG. 19 shows, only modified m-TBA (lane 2) forms a three-component complex (i.e., m-TBA:thrombin:trypsin).

EXAMPLE 16

Streptavidin Hemin Binding Apta-Chelamer

Figure 27:
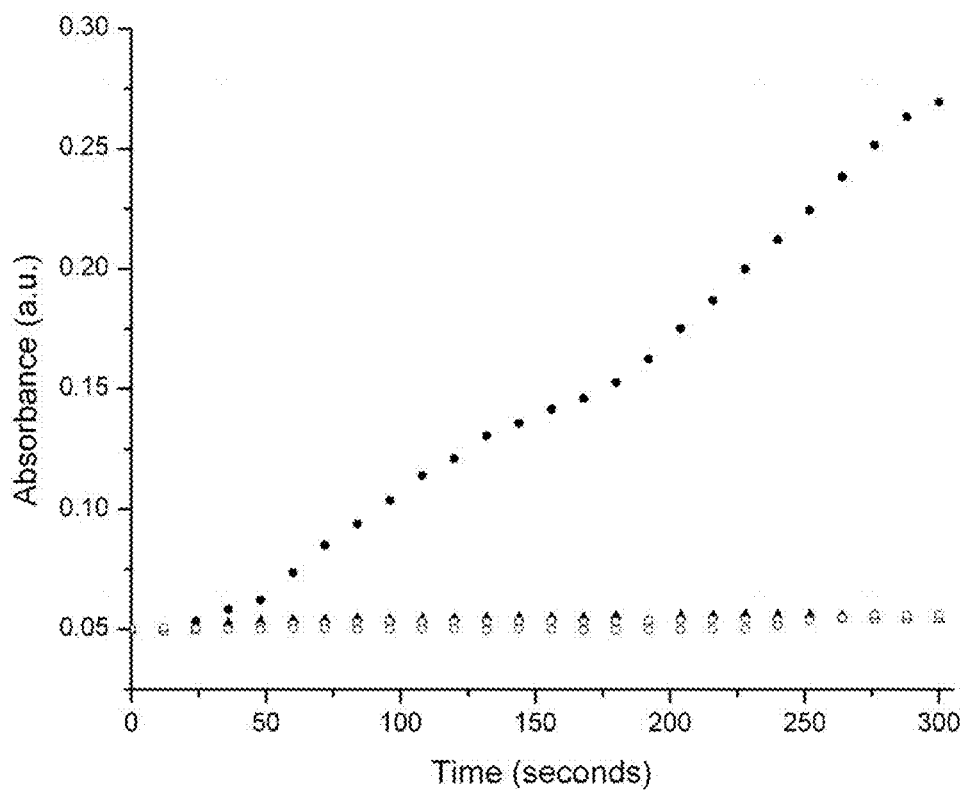
FIG. 27 shows absorbance change at 414 nm of streptavidin immobilized micro-well plates. Micro-wells were incubated for one hour with sample solution in 50 mM HEPES, 20 mM KCl, 200 mM NaCl, 1% DMSO, 0.05% Triton X-100, pH 8.0. AC X1, HBA (hemin binding aptamer), hemin 5 uM, buffer blank. AC X1 and HBA were pre-annealed from 95 C then incubated for 30 minutes with 5 uM hemin. 5 uM AC X1 (●), 5 uM HBA (▲), 5 uM hemin (◇), buffer blank (○).

To demonstrate that aptamers tethered to synthetic protein-binding elements can result in an AC that can signal the presence of the target protein, the present inventor prepared AC-X1 (Formula 9). Here, the core aptamer domain is the catalytically active hemin binding aptamer (HBA; SEQ ID NO:9). AC-X1 incorporates biotin as a small molecule handle for streptavidin. As shown in FIG. 27, the AC-X1 incubated well exhibited a greater absorbance change versus the control HBA well (without streptavidin binding domain). This difference is attributed to the fact that AC-X1 remained in the well, causing the spectroscopically-observed oxidation of ABTS (2,2'-azino-bis(3-ethylbenzthiazoline-6-sulphonic acid)) to ABTS$^+$ (ABTS$_{ox}$).

Formula 9

[Structure: biotin connected via linker to 5'-TGGGTAGGGCGGGTTGGGT-3']

As shown schematically in FIG. 28, streptavidin-immobilized, NUNC 96 well microplates were obtained from Thermo Fisher Scientific. Each well was pre-washed three times with 100 μL of PBS buffer (20 mM NaH$_2$PO$_4$, 30 mM Na$_2$HPO$_4$, 100 mM NaCl, pH 7.4). To each well, 100 μL of sample ODNs (5 μM, previously annealed from 95° C.) with hemin (5 μM) in Hepes buffer (50 mM HEPES, 20 mM KCl, 200 mM NaCl, 1% DMSO, 0.05% Triton X-100, pH 8.0) was incubated for one hour with gentle agitation. Sample ODN solutions were then removed by inversion, and each well washed three times with PBS buffer. Plate wells were then refilled with 98.5 μL of the Hepes buffer containing ABTS (2,2'-azino-bis(3-ethylbenzthiazoline-6-sulphonic acid)). Hydrogen peroxide (2 mM) was then introduced to each well bringing the total assay volume to 100 μL and total ABTS concentration to 2 mM. Visible light absorbance at 414 nm was then immediately followed on a Molecular Devices SpectraMax 190 microplate reader (FIG. 27).

The selection of aptamer cores depends upon the application. For instance, the thrombin responsive (SEQ ID NO:1) tryptase binding aptamer bearing 3-aminomethyl benzenesulfonyl binding units at its 5' and 3' ends (FIG. 6A) is especially attractive because both thrombin and tryptase are up-regulated in a variety of inflammatory diseases. Reed, C. E.; Kita, H. K. "The role of protease activation of inflammation in allergic respiratory diseases" J. Allergy. Clin. Immunol. 2004, 114, 997-1008, incorporated by reference herein in its entirety. Thus inhibiting tryptase activity in the presence of aptamer-bound thrombin may provide a dual pronged approach to the treatment of chronic inflammation. On the other hand, a hemin responsive aptamer core would be advantageous in developing a colorimetric detection assay for tryptase.

Figure 5C:
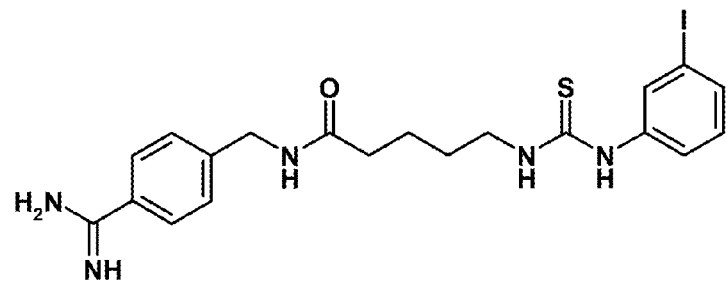
FIG. 5C shows a trypsin inhibitor.

Bidentate binding to a target protein is not only generally expected to increase the affinity constant, it is also anticipated to enhance the binding selectivity. Furthermore, by modifying the nature of synthetic protein binding elements as well as the length of the spacer groups, apta-chelamers that can bind selectively to these other proteases will be developed. For example, the heterobifunctional molecule of FIG. 5C, which incorporates benzamidine and iodophenylthiourea moieties, exhibits an IC$_{50}$ of 0.8 μM for trypsin inhibition. Melkko, S.; Zhang, Y.; Dumelin, C. E.; Scheuermann, J.; Neri, D. "Isolation of high-affinity trypsin inhibitors from a DNA-encoded chemical library" Angew. Chem. Int. Ed. 2007, 46, 4671-4674, incorporated by reference herein in its entirety. This molecule was recently developed by Neri and coworkers from a DNA-encoded chemical library using synthetic protein binding elements appended on duplex DNA (see, e.g., FIG. 3A).

In a similar fashion, appropriate functionalization of aptamer termini with synthetic protein binding groups that target two distinct sites on thrombin will lead to stimulus-responsive inhibitors of thrombin (FIG. 29). Here, the protein binding modules will target the active site, as well as the fibrinogen recognition exosite of thrombin. Skordalakes, E.; Elgendy, S.; Goodwin, C. A.; Green, D.; Scully, M. F.; Kakkar, V. V.; Freyssinet, J.-M.; Dodson, G.; Deadman, J. J. "Bifunctional peptide boronate inhibitors of thrombin: Crystallographic analysis of inhibition enhanced by linkage to an exosite 1 binding peptide" Biochemistry 1998, 37, 14420-14427, incorporated by reference herein in its entirety. Importantly, the thrombin responsive aptamer core (SEQ ID NO:6) will be used, resulting in a stimulus activated protein binder that is activated by the same target protein (FIG. 29). Such an allosteric system will serve as an important model for more complex cooperative proteins such as hemoglobin.

Apta-chelamers that sequester critical proteins involved in the pathogenesis of *tuberculosis* (TB) will also be developed. The first target will be the PPE family of proteins that have been linked to TB virulence. Li, Y.; Miltner, E.; Wu, M.; Petrofsky, M.; Bermudez, L. E. "A *mycobacterium avium* PPE gene is associated with the ability of the bacterium to grow in macrophages and virulence in mice" Cell. Microbiol. 2005, 7, 539-548, incorporated by reference herein in its entirety. Recently, Eisenberg and coworkers used protein co-crystallization studies to demonstrate that a PPE protein interacts with the PE protein (another member of the TB proteome) through the formation of a stable four-helix bundle. Strong, M.; Saway, M. R.; Wang, S.; Phillips, M.; Cascio, D.; Eisenberg, D. "Toward the structural genomics of complexes: crystal structure of a PE/PPE protein complex from *mycobacterium tuberculosis*" Proc. Natl. Acad. Sci. USA. 2006, 103, 8060-8065, incorporated by reference herein in its entirety. Both proteins (PPE and PE) contribute two α-helices to form this complex. The driving force for this protein-protein interaction, which is suggested to be important in TB signal transduction, is the burial of apolar side chains into the interface of the helix bundle. Furthermore, the distance between the intramolecular helices of the PE protein is ~11 Å. This gap corresponds favorably with the distance between the 5' and 3' termini of the aforementioned quadruplex-forming aptamers. Therefore, apta-chelamers that can block this critical protein-protein interaction and serve as detection agents for PPE will be developed. Specifically, the two α-helix forming peptides from the PE protein (which participate in forming a complex with PPE) will be attached to spacer moieties, which in turn are attached to the 5' and 3' ends of the hemin responsive aptamer core. It is expected that a two-helix bundle (comprising the attached PE protein α-helices) will form upon association of the aptamer to hemin. The resulting activated complex of FIG. 6C, is expected to bind to the PPE protein via protein-protein interactions (FIG. 6C). This aspect of the present invention is particularly important because there is an urgent (yet unmet) need for effective detection methods for TB.

EXAMPLE 17

Hemin Responsive Apta-Chelamer: Generation and Selection of Bidentate Binders A second aptamer that can be used is the 17-mer hemin responsive aptamer, with sequence 5'-GGGTAGGGCGGGT-TGGG-3' (SEQ ID NO:10). Appropriate modification of this aptamer by addition of two dTs (one for each terminus) results in the ODN domain for AC 14, with sequence 5'-TGGGTAGGGCGGGTTGGGT-3' (SEQ ID NO:9, and shown schematically in FIG. 4). This DNA sequence, when bound to hemin (in the presence of $K^+$) is capable of folding into a stable intramolecular quadruplex (FIG. 4). Chinnapen, D. J. F.; Sen, D. "Hemin-stimulated docking of cytochrome c to a hemin-DNA aptamer complex" Biochemistry 2002, 41, 5202-5212, incorporated by reference herein in its entirety. Moreover, this aptamer sequence is particularly attractive because the hemin-bound aptamer acts as a horseradish peroxidase mimic (see, e.g., Travascio, P.; Sen, D.; Bennet, A. J. "DNA and RNA enzymes with peroxidase activity—an investigation into the mechanism of action" Can. J. Chem. 2006, 84, 613-619, incorporated by reference herein in its entirety.) and thus can be used as a colorimetric sensor (i.e., via the production of oxidized 2,2'-azino-bis(3-ethylbenzthiazoline-6-sulfonic acid) or ABTS). Attachment of appropriate synthetic binding elements to the 5' and 3' termini of this aptamer chimera results (in the presence of $K^+$ and hemin) in an activated molecule that can be used as a detection platform for various bidentate target proteins (FIG. 30).

Figure 30:
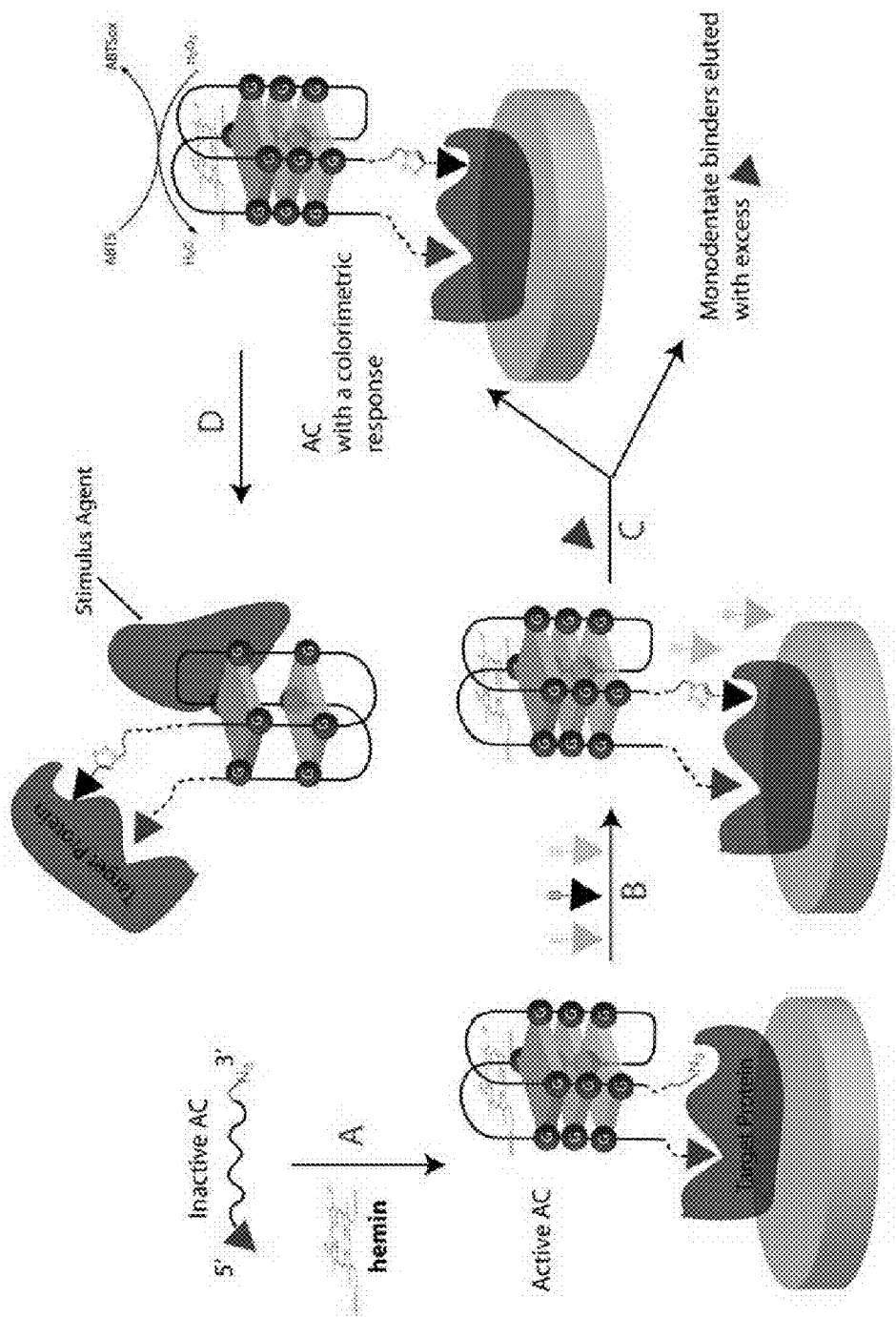
FIG. 30 is a schematic illustrating the development of high affinity ACs against a selected target protein. Heroin has an iron (Fe) atom (not shown) in the center of the macrocycle, and a chloride counter anion (also not shown).

As seen in FIG. 30, pathway A, allosteric activation of AC x in the presence of hemin (and potassium) results in the formation of an activated AC x2 through intramolecular guanine quadruplex formation. Addition of AC x2 to microwells coated with target protein results in the binding of AC x2 to the protein via one arm (i.e., the known fragment (triangle)). The antiparallel quadruplex formation of AC x2 will necessitate the positioning of the second arm (which contains an azide terminus) close to the target protein. Following pathway B, addition of a library of secondary synthetic fragments (fletched triangles) that contain an alkyne group followed by a 'click' reaction will lead to covalent tethering of these secondary protein-binding fragments onto the AC arm. The triazole forming reaction will have a large preference for small-molecules that bind to a secondary site on the protein due to proximity ligation effects. Along pathway C, washing the system with excess known small-molecule (triangle) will remove any monodentate binders. Microwells containing bidentate binders (for e.g. AC x3) will be detected by exploiting a colorimetric response from the AC (i.e., production of oxidized 2,2' azino-bis(3-ethylbenzthiazoline-6-sulfonic acid or ABTS). Following pathway D, identification of the secondary small-molecules and attachment of these ends (through appropriate spacers) onto a central aptamer domain (for e.g., the thrombin binding aptamer is depicted) is expected to result in high affinity ACs against the target protein.

A non-exhaustive list of other aptamers that would be suitable for the methods of the present invention (i.e., upon binding to their cognate targets they would fold into a conformation wherein the 5' and 3' termini are oriented in a directed manner amenable for projection of synthetic protein binding fragments) include: coagulation factor IXa responsive aptamer (SEQ ID NO:11); VegF responsive aptamer (SEQ ID NO:12); TAR (trans-activating element of the HIV-1 genome) responsive aptamer (SEQ ID NO:13); NFκB p50 responsive aptamer (SEQ ID NO:14); U1 snRNA hairpin II responsive aptamer (SEQ ID NO:15); U1 snRNA hairpin IV responsive aptamer (SEQ ID NO:16); TAR HIV 1 (core 31-mer) responsive aptamer (SEQ ID NO:17); TAR BIV (core 28-mer) responsive aptamer (SEQ ID NO:18); HIV-1 RRE (core 35-mer) responsive aptamer (SEQ ID NO:19); AMP responsive aptamer (SEQ ID NO:20); and tobramycin responsive aptamer (SEQ ID NO:21).

In conclusion, the present inventor has developed a "smart" apta-chelamer that is capable of switching from a quadruplex conformation to a duplex form in a cyclical manner upon addition of ODN-derived stimuli. The quadruplex conformation exploits chelate interactions mediated through designed synthetic protein-binders in order to dramatically enhance trypsin-binding.

All references cited in this specification are herein incorporated by reference as though each reference was specifically and individually indicated to be incorporated by reference. The citation of any reference is for its disclosure prior to the filing date and should not be construed as an admission that the present invention is not entitled to antedate such reference by virtue of prior invention.

It will be understood that each of the elements described above, or two or more together may also find a useful application in other types of methods differing from the type described above. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention set forth in the appended claims. The foregoing embodiments are presented by way of example only; the scope of the present invention is to be limited only by the following claims.

---

The invention claimed is:

1. A compound of the formula:

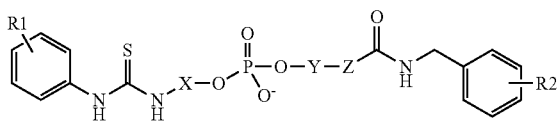

or a tautomeric form thereof, and/or a pharmaceutically acceptable salt thereof, and/or a pharmaceutically acceptable solvate thereof, wherein:
a) R1 represents iodine (—I);
b) X represents —(CH2)$_{n1}$—, wherein n1 represents an integer in the range of from 3 to 15;
c) Y represents an aptamer sequence;
d) Z represents —(CH2)$_{n2}$—, wherein n2 represents an integer in the range of from 3 to 15; and
e) R2 represents acetamidine (—C(=NH)NH$_2$).

2. The compound of claim 1, wherein R1 is in the meta position, and wherein R2 is in the para position.

3. The compound of claim 1, wherein n1 is equal to 6.

4. The compound of claim 1, wherein n2 is equal to 9.

5. The compound of claim 1, wherein Y comprises the nucleic acid sequence set forth in SEQ ID NO:6.

6. The compound of claim 2, wherein n1 is equal to 6, n2 is equal to 9, and Y comprises the nucleic acid sequence set forth in SEQ ID NO:6.

7. The compound of claim 2, wherein n1 is equal to 6, n2 is equal to 9, and Y is the nucleic acid sequence set forth in SEQ ID NO:6.

8. The compound of claim 2, wherein n1 is equal to 6, n2 is equal to 9, and Y is the nucleic acid sequence set forth in SEQ ID NO:1.

9. The compound of claim 2, wherein n1 is equal to 6, n2 is equal to 9, and Y is the nucleic acid sequence set forth in SEQ ID NO:4.

* * * * *